United States Patent [19]

Kimoto et al.

[11] Patent Number: 6,036,971
[45] Date of Patent: Mar. 14, 2000

[54] COATED GRANULAR PESTICIDE METHOD FOR PRODUCING THE SAME AND APPLICATIONS THEREOF

[75] Inventors: Narutoshi Kimoto; Yoshiya Kutsuzawa, both of Kitakyushu; Michiyuki Ashihara, Minamata, all of Japan

[73] Assignee: Chisso Corporation, Osaka, Japan

[21] Appl. No.: 09/000,159

[22] PCT Filed: Jul. 26, 1996

[86] PCT No.: PCT/JP96/02116

§ 371 Date: Jan. 28, 1998

§ 102(e) Date: Jan. 28, 1998

[87] PCT Pub. No.: WO97/04652

PCT Pub. Date: Feb. 13, 1997

[30] Foreign Application Priority Data

| | | | |
|---|---|---|---|
| Jul. 28, 1995 | [JP] | Japan | 7-212910 |
| Aug. 30, 1995 | [JP] | Japan | 7-245485 |
| Sep. 11, 1995 | [JP] | Japan | 7-258184 |
| Oct. 16, 1995 | [JP] | Japan | 7-293663 |
| Feb. 1, 1996 | [JP] | Japan | 8-040658 |
| Feb. 28, 1996 | [JP] | Japan | 8-069018 |
| Apr. 15, 1996 | [JP] | Japan | 8-117046 |
| May 27, 1996 | [JP] | Japan | 8-156094 |
| May 27, 1996 | [JP] | Japan | 8-178644 |
| Jun. 19, 1996 | [JP] | Japan | 8-178644 |
| Jun. 19, 1996 | [JP] | Japan | 8-179965 |

[51] Int. Cl.$^7$ ................................................. A01N 25/26
[52] U.S. Cl. ........................ 424/419; 424/417; 424/490; 424/497
[58] Field of Search ..................... 424/405, 409, 424/417, 419, 489, 490, 497

[56] References Cited

U.S. PATENT DOCUMENTS

| | | | |
|---|---|---|---|
| 4,343,790 | 8/1982 | Pasarela | 424/419 |
| 4,485,103 | 11/1984 | Pasarela | 424/497 |
| 5,310,785 | 5/1994 | Hayakawa et al. | 525/7 |
| 5,441,923 | 8/1995 | Tocker | 504/125 |

FOREIGN PATENT DOCUMENTS

| | | |
|---|---|---|
| 63-147888 | 6/1988 | Japan . |
| 01(1989)-05002 | 1/1989 | Japan . |
| 02-286602 | 11/1990 | Japan . |
| 05-004887 | 1/1993 | Japan . |
| 06-009303 | 1/1994 | Japan . |
| 06-009304 | 1/1994 | Japan . |
| 06-056567 | 3/1994 | Japan . |
| 06-072805 | 3/1994 | Japan . |
| 06-080514 | 3/1994 | Japan . |

*Primary Examiner*—Robert H. Harrison
*Attorney, Agent, or Firm*—McDermott, Will & Emery

[57] ABSTRACT

A coated granular pesticide comprising a granular pesticide for use on plants which comprises at least one hardly water-soluble active ingredient and at least one water-swelling substance, and a thermoplastic resin-based film which covers the surface of the granular pesticide; a method for producing the same; and applications thereof. A surfactant, inorganic powder insoluble or hardly soluble in water, water-absorbing and/or water-soluble polymer fine powder, a thermosetting resin, or a biodegradable polymer insoluble or hardly soluble in water, or a combination thereof may be incorporated into the film. The coated granular pesticide can externally release the hardly water-soluble active ingredient due to the combined effects of the thermoplastic resin as the film-forming component and the water-swelling component as the core component whereby the water-swelling substance absorbs the water present in the exterior of the coated granular pesticide, which gradually penetrates into the granule through the coating film.

14 Claims, 8 Drawing Sheets

Micrographs Showing Coated Granular Pesticide 1

Fig. 1-A
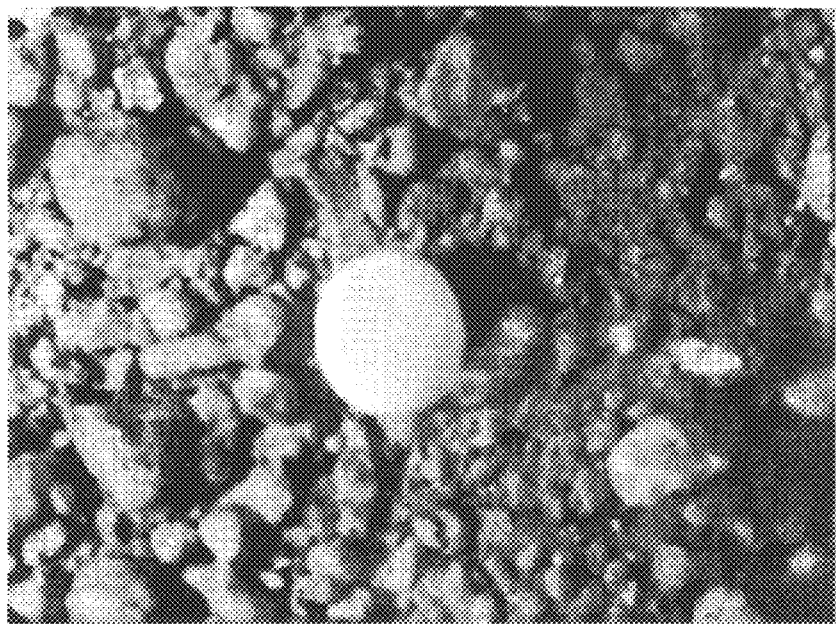
Fig. 1-B
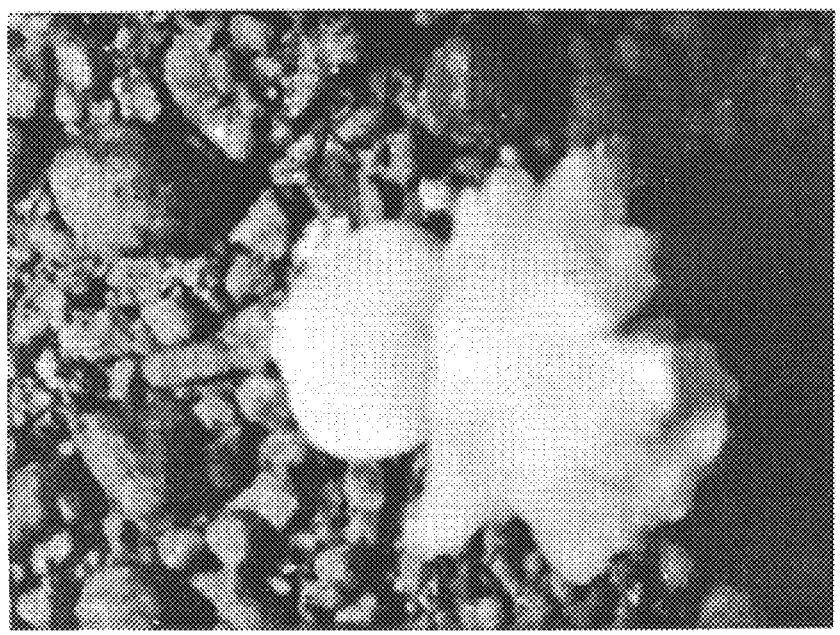
Micrographs Showing Coated Granular Pesticide 1

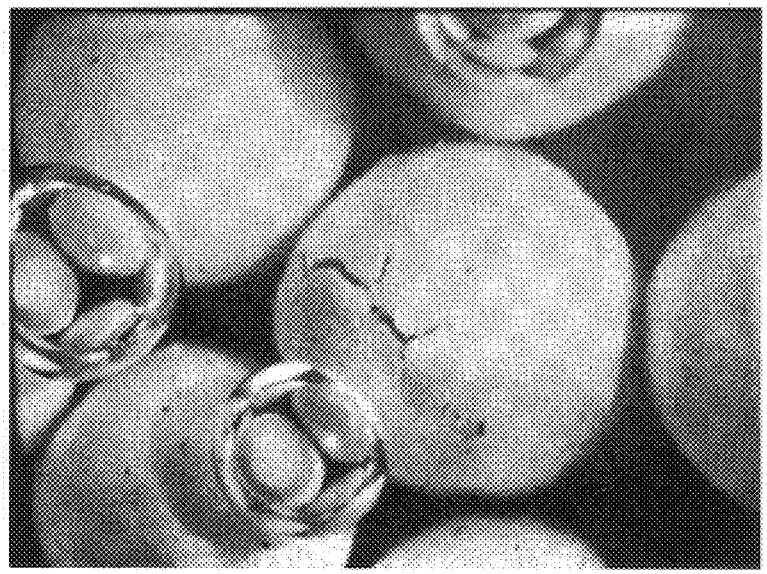
Fig. 3-A
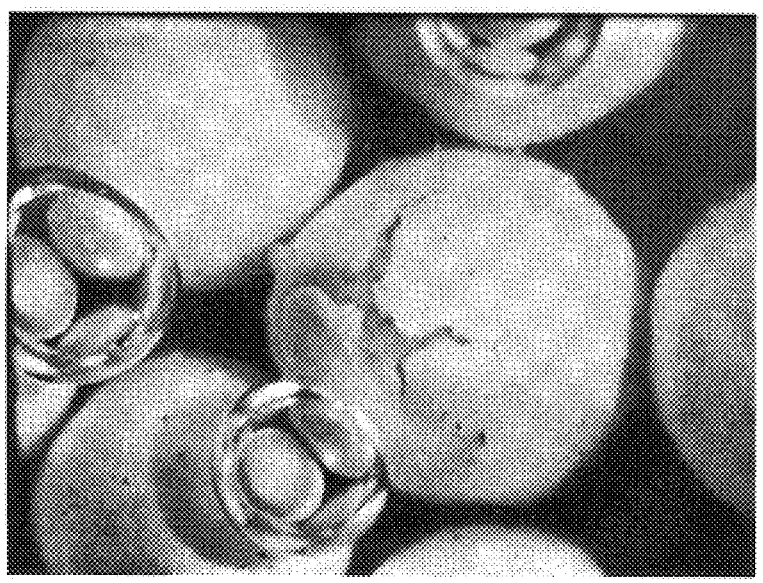
Fig. 3-B
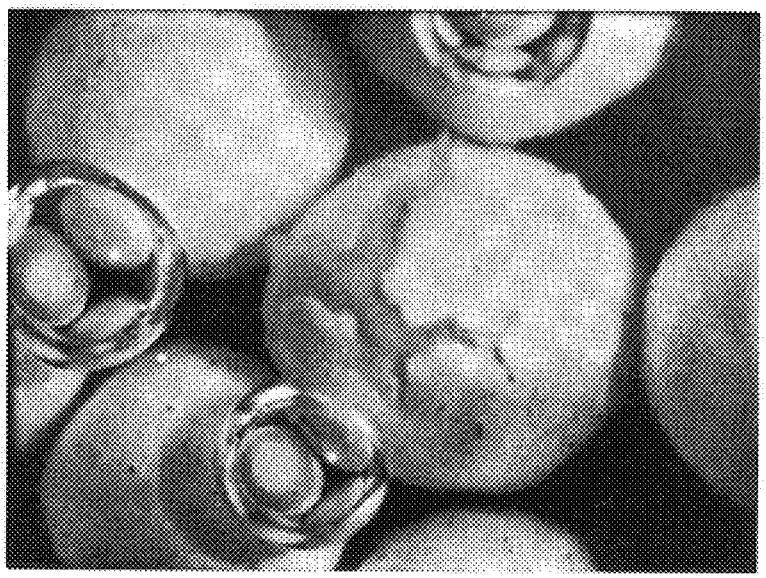
Fig. 3-C

COATED GRANULAR PESTICIDE METHOD FOR PRODUCING THE SAME AND APPLICATIONS THEREOF

TECHNICAL FIELD

The present invention relates to a timed-release type or controlled release type pesticide. More specifically, the present invention pertains to a coated granular pesticide comprising a granular pesticide which comprises a hardly water-soluble active ingredient and a water-swelling substance and whose surface is covered with a film-foaming material comprising a thermoplastic resin as a principal component, a method for producing the same and a method for using the coated granular pesticide.

BACKGROUND ART

The use of insecticides, fungicides or herbicides has been indispensable to the cultivation of field crops. When applying a pesticide, it is preferably applied in a large amount at a time from the viewpoint of the reduction of labor required for the application thereof, but such application suffers from various problems such that crops and human bodies are damaged by such a high concentration of the active ingredient, that the active ingredient is lost through washing away and that the duration of the efficacy thereof is correspondingly reduced.

In case of the crops which require the transplantation of the seedling such as those represented by paddy rice, they are damaged upon transplantation, for instance, by cutting of hair-roots and breakage of the seedlings. Moreover, the seedlings after the transplantation are in an unstable state till complete rooting thereof because of the great difference between the environmental conditions of nursery beds and final fields. For this reason, the application of a pesticide possessing a herbicidal action at this stage may bring about hypotrophy and withering of seedlings due to its phytotoxity.

If a pesticide such as a herbicide may be applied to seedlings when transplanting the seedlings, the labor required for farm working can effectively be reduced. In case of paddy rice, however, any herbicide can be applied thereto only after the complete rooting of the seedlings, i.e., after the lapse of about one week from the transplanting the seedlings, under the existing circumstances.

There have been known a variety of sustained release pesticides which are developed for eliminating such drawbacks and are so designed that active ingredients are gradually released from those applied to fields.

Japanese Patent Laid-Open Publication (JP-A) 286602/1990 discloses a granular controlled release pesticide which comprises mineral particles impregnated with a liquid active ingredient and hydrophobic fine particles which cover the surface of the mineral granules. However, the controlled release pesticide initiates the release of the active ingredient thereof immediately after the application thereof to fields and accordingly, it is not suitably applied to fields during the transplantation of seedlings.

Japanese Examined Patent Publication (JP-B) 5002/1989 discloses a sustained release pesticide which comprises a water-soluble or volatile active ingredient covered with a thermoplastic resin. In the controlled release pesticide, the active ingredient is released through the thermoplastic resin film. Therefore, this technique is suitable for water-soluble or volatile active ingredients, but it is difficult to apply the technique to hardly water soluble active ingredients. In general, most of the active ingredients used in herbicides are hardly soluble in water and if these active ingredients are covered with the films disclosed in JP-B 5002/1989, the resulting pesticide suffers from such problems that a desired herbicidal effect cannot be expected because of its extremely low release rate and that the active ingredient remains in the soil even after the harvesting of crops to thus cause contamination of the soil therewith.

JP-A 9304/1994 and JP-A 72805/1994 disclose timed-release, controlled release type pesticides, in which a part of the coating film is dissolved, after the application thereof to fields, to form openings through which the active ingredient is released. Moreover, JP-A 9303/1994 and JP-A 80514/1994 also disclose timed-release, controlled release type pesticides, in which the active ingredient is released through cracks formed, after the application thereof to fields, on a part of the coating film. In these timed-release, controlled release type pesticides, however, the timed-release characteristics are achieved by the use of a coating film having a double layered structure and the method for the production thereof requires complicated steps and the resulting product is expensive. Moreover, since the active ingredient is released through small openings or cracks formed on the film, the release rate thereof is show and thus it is difficult to apply these techniques to hardly water-soluble active ingredients.

The present invention intends to eliminate the foregoing drawbacks associated with the existing controlled release pesticides and accordingly, it is an object of the present invention to provide a coated granular pesticide which does not release any active ingredient immediately after the application thereof to fields and initiates the release of the active ingredient after the lapse of a desired period of time and which can complete the release of the active ingredient during the cultivation period, in particular, those effectively applied to hardly water-soluble active ingredients. It is another object of the present invention to provide a method for producing the same and a method for using the same.

DISCLOSURE OF THE INVENTION

The inventors have conducted extensive studies in order to accomplish the foregoing objects, and have found out that the desired objects can be achieved by a coated granular pesticide which comprises a granular pesticide comprising a hardly water-soluble active ingredient and a water-swelling substance, whose surface is coated with a film mainly comprising a thermoplastic resin. On the basis of this finding, the present invention has been completed.

As the thermoplastic resin of the coating film, it is preferred to use at least one polymer selected from the group consisting of olefinic polymers and olefinic copolymers comprising an olefin as a major monomer.

The coating film preferably comprises not more than 15% by weight of an ethylene/vinyl acetate copolymer. It is also preferred that the coating film comprises a surfactant, an powdery inorganic substance insoluble or hardly soluble in water, a water-absorbing and/or water-soluble fine polymer powder, a thermosetting resin or a biodegradable polymer insoluble or hardly soluble in water, which may be used alone or in any combination.

BRIEF DESCRIPTION OF THE DRAWINGS

FIGS. 1-A and 1-B are photographs of the coated granular pesticide according to the present invention before and after the breakage of the coating film, respectively;

FIGS. 3-A to 3-C are photographs for ilustrating the breakage of the coating film of the coated granular pesticide 2 with time, respectively;

Figure 2:
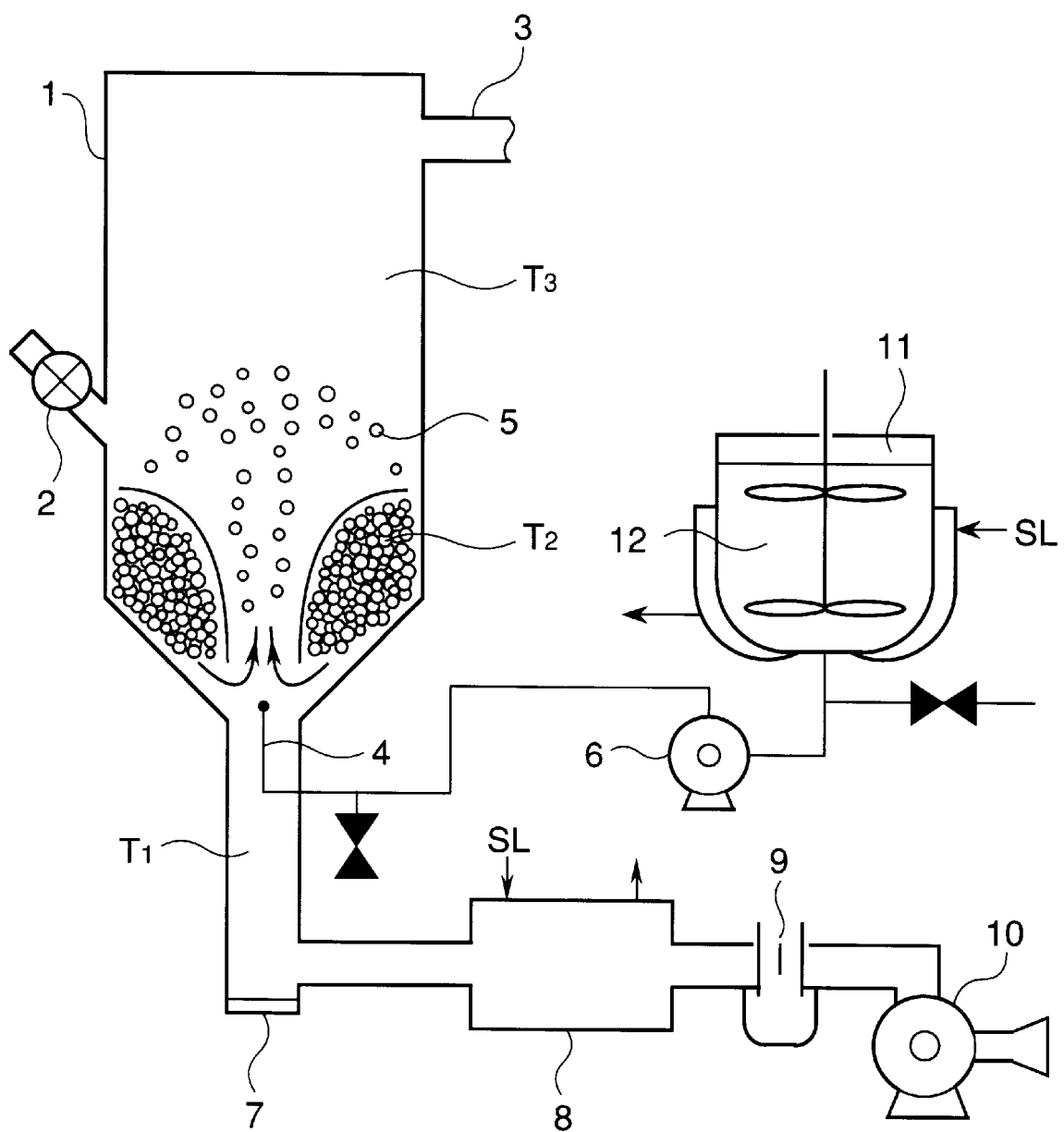
FIG. 2 is a schematic diagram illustrating an embodiment of a preferred apparatus which can be used in the production of the coated granular pesticide according to the present invention.

1 spouting column;
2 opening for introducing granules;
3 outlet for exhaust gas;
4 spray nozzle;
5 granular pesticide;
6 pump;
7 opening for withdrawal;
8 heat exchanger;
9 orifice flowmeter;
10 blower;
11 dissolution tank;
12 mixed solution of film-forming materials;
$T_1$ temperature of flowing gas;
$T_2$ temperature of granular pesticide;
$T_3$ temperature of exhaust gas;
SL steam

BEST MODE FOR CARRYING OUT THE INVENTION

The present invention will hereinafter be described in more detail.

The coated granular pesticide according to the present invention is a timed-release, sustained release type coated granular pesticide which does not release externally the hardly water-soluble active ingredient included in the granular pesticide within a predetermined period of time till the coating film is disintegrated, but the active ingredient is gradually and externally released after once the disintegration of the film is initiated.

More specifically, in the coated granular pesticide according to the present invention, water present in the external environment penetrates into the inside of the coated granular pesticide through the coating film, where the water-swelling substance gradually absorbs the water to swell and grow its volume, thereby applying increasing stress to the coating film. When the stress due to the swelling exceeds the threshold stress of the coating film, cracks are formed on the film, through which water rapidly enters into the coated pesticide to accelerate the swelling of the water-swelling substance and thus to grow the cracks thereby rapidly disintegrating the coating film. Consequently, the hardly water-soluble active ingredient included in the granular pesticide comes in close contact with a large amount of water and as a result, the release of the hardly water-soluble active ingredient is initiated.

Photographs illustrating the breakage of the film of the coated granular pesticide according to the present invention are shown in FIG. 1. More specifically, FIG. 1-A and FIG. 1-B are photographs showing the coated granular pesticide 1 prior to and after the breakage of the coating film.

The present invention makes it possible to control the time required for the disintegration of the film and the initiation of the release of the hardly water-soluble active ingredient after the application of the coated granular pesticide (hereinafter referred to as "film-disintegration time"). To this end, it is important to take into consideration the moisture permeability of the film, the critical strength of the film and the swelling ability of the granular pesticide.

The moisture permeability of the film is greatly affected by the film-forming components, namely the thermoplastic resin used as a principal ingredient for the film and other components optionally incorporated such as surfactants, powdery inorganic substances, water-absorbing polymer fine particles, water-soluble polymer fine particles, thermosetting resins and/or hardly water-soluble or water-insoluble biodegradable polymers. The critical strength of the film is substantially dependent upon the film-forming components and the thickness of the film, for example, the kinds of thermoplastic resins used, the thickness and the uniformity of the film. The swelling properties of the granular pesticide vary depending on the kinds of the water-swelling substances as an ingredient of the granular pesticide.

According to the present invention, the film-disintegration time as defined above can be elongated by combining a thick and uniform film having high critical strength and poor moisture permeability with a water-swelling substance having poor swelling properties. On the other hand, the film-disintegration time can be reduced by combining a thin and uneven film having low critical strength and excellent moisture permeability with a water-swelling substance having good swelling properties.

In particular, the film-disintegration time is susceptible to the moisture permeability of the film and therefore, special attention should be paid to the control of the moisture permeability of the film.

If the moisture permeability of the film is extremely high, the water-swelling substance may rapidly swell and the film may be disintegrated almost at the same time when the coated granular pesticide is applied to a water-rich area such as a paddy field.

According to the present invention, various coated granular pesticides adapted for crops to which they are pplied and cultivating conditions of the crops can be obtained by appropriately controlling the moisture erasability and critical strength of such a film and the water-swelling properties of the granular pesticide.

The coated granular pesticide according to the present invention comprises, as an active ingredient, a hardly water-soluble active ingredient having an insecticidal, fungicidal or herbicidal effect or a plant growth regulating effect. In addition, the hardly water-soluble active ingredient may be a single ingredient or a combination of a plurality of ingredients and the kinds of the ingredients and combinations thereof are not particularly restricted to specific ones.

The term "hardly water-soluble active ingredient" herein used means those having a solubility in water of not more than 1000 ppm (at 20° C.). In the present invention, preferably used are hardly water-soluble active ingredients having a solubility in water of not more than 1000 ppm (at 25°

C.), in particular, not more than 600 ppm and more preferably not more than 50 ppm.

In this respect, if using an active ingredient having a higher solubility in water, a large amount of the active ingredient is released at the initial stage when the coated granular pesticide initiates the release of the active ingredient, and thus the chemical injury of crops can be caused and the sustained release effect of the pesticide cannot be attained.

Specific examples of the hardly water-soluble active ingredients usable herein are 1-(6-chloro-3-pyridylmethyl)-N-nitroimidazolidine-2-ylideneamine, 5-methyl-1,2,4-triazolo(3,4-b)benzothiazole, 3-allyloxy-1,2-benzoisothiazole-1,1-dioxide, 2-chloro-4-ethylamino-6-isopropylamino-s-triazine, 1-(2-chloroimidazo[1,2-a]pyridin-3-ylsulfonyl)-3-(4,6-dimethoxypyrimidin-2-ylurea, 2-chloro-4,6-bis(ethylamino)-s-triazine, 2-benzothiazol-2-yloxy-N-methylacetoanilide, methyl=-α-(4,6-dimethoxypyrimidin-2-ylcarbamoylsulfamoyl)-o-toluate, S-(4-chlorobenzyl)-N,N-diethylthiocarbamate, S-benzyl=1, 2-dimethylpropyl(ethyl)thiocarbamate, 2,4-dichlorophenyl-3'-methoxy-4'-nitrophenyl ether, 2-methylthio-4-ethylamino-6-(1,2-dimethylpropylamino)-s-triazine, 4-(2,4-dichlorobenzoyl)-1,3-dimethyl-5-pyrazolyl-p-toluenesulfonate, 2-methylthio-4,6-bis(ethylamino)-s-triazine, S-1-methyl-1-phenylethyl=piperidine-1-carbothioate, 1-(α, α-dimethylbenzyl)-3-(p-tolyl) urea, 2-chloro-N-(3-methoxy-2-tenyl)-2',6'-dimethylacetoanilide, 2-chloro-2',6'-diethyl-N-(butoxymethyl)acetoanilide, ethyl 2,4-dichlorophenoxy acetate, ethyl 2-methyl-4-chlorophenoxy acetate, (E)-(S)-1-(4-chlorophenyl)-4,4-dimethyl-2-(1H-1,2,4-triazol-1-yl)pent-1-en-3-ol, (2RS, 3RS)-1-(4-chlorophenyl)-4,4-dimethyl-2-(1H-1,2,4-triazol-1-yl)pentan-3-ol and 4'-chloro-2'-(α-hydroxybenzyl) isonicotinanilide.

The water-swelling substance used in the coated granular pesticide according to the present invention is a substance capable of undergoing a volume-expansion through absorption of water and examples thereof include bentonites, starches and highly water-absorbing polymers.

As has been well-known in the art, the water-swelling properties of bentonite vary depending on the composition and particle size thereof. Any particular problem does not arise even when using, for example, calcium type bentonite which is rich in calcium ions and magnesium ions and has a low swelling ability and activated type bentonite which is treated with soda to artificially impart the swelling activity, but preferred are sodium type bentonite which has a high swelling ability, i.e., which is capable of absorbing a large amount of water.

Examples of starches are naturally occurring starches such as corn starch and potato starch; and a variety of processed starch products such as oxidized starches, methylated starches and carboxymethylated starches.

Examples of highly water-absorbable polymers include highly water-absorbable cellulosic polymers, highly water-absorbable polyvinyl alcoholic polymers and highly water-absorbable acrylic polymers.

These water swelling substances may be used alone or in any combination and the kinds and combinations thereof are not restricted to specific ones.

In the present invention, the foregoing hardly water-soluble active ingredient and the foregoing substance having a water-swelling ability are mixed together to give a granular pesticide. The granular pesticide preferably has a particle size ranging from 0.5 to 10 mm and more preferably 1 to 5 mm. Such a granular pesticide is obtained through granulation according to the currently used method, but may easily be produced using granulation through extrusion. Moreover, in this respect, the foregoing granular pesticide can easily be produced if an auxiliary agent for granulation and/or a binder are used during the granulation.

Examples of auxiliary agents for granulation include powdery inorganic substances such as clay, kaolin and vermiculite powder; powdery organic substances such as powdered rice husk; and fertilizers such as urea, ammonium sulfate and ammonium chloride.

Examples of binders are gum arabic, carboxymethyl cellulose, hydroxyethyl cellulose and polyvinyl alcohol.

In the present invention, the foregoing granular pesticide is covered with a film mainly comprising a thermoplastic resin.

The thermoplastic resin used as a principal component for the film is preferably resins having low water permeability and specific examples thereof include olefinic polymers such as polypropylene, polyethylene, polybutene and polystyrene; olefinic copolymers mainly comprising olefins such as ethylene/propylene copolymer, ethylene/carbon monoxide copolymer, butene/ethylene copolymer, butene/propylene copolymer, ethylene/vinyl acetate copolymer, ethylene/vinyl acetate/carbon monoxide copolymer, ethylene/acrylic acid copolymer and ethylene/methacrylate copolymer; vinylidene chloride type copolymers such as vinylidene chloride/vinyl chloride copolymer; diene type polymers such as butadiene polymer, isoprene polymer, chloroprene polymer, butadiene/styrene copolymer, EPDM polymer and styrene/isoprene copolymer; and waxes such as bees wax, haze wax and paraffins. Among these thermoplastic resins, preferred are olefinic polymers and olefinic copolymers mainly comprising olefins.

These thermoplastic resins may be used alone or in any combination of at least two of them. In addition, they may optionally be used in combination with natural resins such as naturally occurring gums and rosins; fats and oils; and/or modified fats and oils. The kinds and combinations thereof are not restricted to any specific one.

Thermoplastic resins each having a high elastic modulus such as ethylene/vinyl acetate copolymer, ethylene/vinyl acetate/carbon monoxide copolymer and diene type polymers may serve to control the film-disintegration time since the resins can impart flexibility to the film and has an effect of relieving the internal stress due to the swelling of the granular pesticide, but if these polymers are present in the film in a large amount, the film-disintegration time may extremely be prolonged and the resulting film may not form cracks. Therefore, the amount of the polymer to be incorporated into the film is preferably less than 20% by weight and more preferably not more than 15% by weight.

In the present invention, a surfactant may be added to the film to control the moisture permeability of the film and to thus control the disintegration time of the resulting film of the coated granular pesticide. The surfactant permits the improvement of the moisture permeability of the film and accordingly, shows an effect of reducing the film-disintegration time. The moisture permeability of the resulting film is sometimes reduced to a level practically acceptable depending on the kinds of the thermoplastic resins used for forming the film and cracks may be formed with difficulty. The use of a surfactant is quite effective in such cases.

The surfactants usable herein suitably have an HLB value ranging from 6 to 20, preferably 9 to 16 and more preferably 11 to 13. In this regard, the hydrophilicity of the surfactant is increasingly strong as the HLB value thereof exceeds 20. For this reason, such a surfactant cannot uniformly be dispersed in the resulting film and this may become a cause of defects of the film. On the other hand, if the surfactant used is highly lipophilic and has an HLB value of less than 6, it may sometimes be impossible to achieve an intended effect of increasing the moisture permeability of the film to thus reduce the film-disintegration time.

The surfactant usable herein may be anionic, cationic, nonionic and amphoteric surfactants, which may be used alone or as a mixture of a plurality of these surfactants while adjusting the HLB value to the level falling within the range defined above. In the present invention, particularly preferred are nonionic surfactants.

Examples of anionic surfactants are higher fatty acid salts, higher alkyl dicarboxylic acid salts, sulfuric acid ester salts of higher alcohols, higher alkyl-sulfonic acid salts, higher alkyl-disulfonic acid salts, sulfonated higher fatty acid salts and higher alkyl phosphoric acid ester salts; examples of cationic surfactants are higher alkyl-amine salts and quaternary ammonium salts; and examples of nonionic surfactants are fatty acid esters of polyols and polyethylene oxide condensates. In addition, examples of amphoteric surfactants are betaine type, glycine type, alanine type and sulfobetaine type ones.

Among these surfactants, preferred are, for instance, polyoxyethylene alkyl allyl ethers, polyoxyethylene alkyl ethers and polyoxyethylene alkyl phenyl ethers.

The amount of the surfactants to be added to the film preferably ranges from 0.01 to 20% by weight and more preferably 0.05 to 10% by weight, on the basis of the total weight of the film. This is because if the amount thereof is less than 0.01% by weight, it is difficult to achieve the intended effect of the surfactant used, while the use thereof in an amount of more than 20% by weight is unfavorable from the economical standpoint.

The molecular weight of the surfactant preferably ranges from 100 to 1000.

Moreover, the film used in the present invention may further comprise a powdery inorganic substance for the purpose of adjusting the film-disintegration time of the resulting coated granular pesticide. Powdery inorganic substances show an effect of reducing the film-disintegration time. The powdery inorganic substances usable herein are preferably those insoluble or hardly soluble in water. Specific examples thereof are talc, clay, metal oxides, silicate mineral powder, glass, carbonates or sulfates of alkaline earth metals and sulfur.

These powdery inorganic substances must completely be embedded in the resulting film and accordingly, those having a particle size smaller than the thickness of the film. For instance, the particle size thereof is preferably not more than 50 μm and more preferably 1 to 20 μn. The amount of the inorganic powder to be added to the film is preferably not less than 50% by weight on the basis of the total weight of the film, but it is not particularly restricted to this specific range.

The coated granular pesticide may comprise, in the film, fine particles of a water-absorbing polymer and/or a water-soluble polymer in order to adjust the film-disintegration time of the pesticide. These fine particles of water-absorbing and/or water-soluble polymers show an effect of reducing the film-disintegration time of the film.

Examples of fine particles of water-absorbing and/or water-soluble polymers are fine particles of polyvinyl alcohol, polyvinylpyrrolidone, methyl cellulose, hydroxypropyl cellulose, hydroxyethyl cellulose, sodium carboxymethyl cellulose, hydroxypropylmethyl cellulose, calcium carboxymethyl cellulose, carboxymethylethyl cellulose, dextrin, alginates, gelatin, pectin, pullulan, polyacrylic acid, sodium polyphosphate, isobutylene copolymers and polyethylene oxide.

The particle size of these fine particles ranges from 0.1 to 100 μm and preferably 0.5 to 50 μm. If the particle size is greater than 100 μm, they cannot easily be dispersed in the film. On the other hand, it is difficult to prepare a synthetic polymer having a particle size of less than 0.1 μm, and such a polymer cannot show its characteristic properties.

The amount of these fine particles to be added to the film preferably ranges from 0.1 to 30% by weight on the basis of the total weight of the film.

The coated granular pesticide of the present invention may further comprise, in the coating film, a thermosetting resin for the purpose of controlling the film-disintegration time of the coated granule. Such a thermosetting resin shows an effect of reducing the film-disintegration time of the resulting film.

Examples of such thermosetting resins are those obtained through reactions of acid anhydrides with amines and/or diamines such as polyamide, polyimide, bismaleimide, polyamideimide, polyetherimide, maleimide and polyetheramide.

These thermosetting resins used herein may be in any form such as a solution, powder or an intermediate thereof. For instance, the thermosetting resin in a powdery state which can be used in the invention may be prepared by heat conditions of the soil in addition to the hydrolysis by the foregoing hydrolases.

In case of the coated granular pesticide whose coating film comprises such a biodegradable polymer hardly soluble or insoluble in water, the cleavage of the backbone chain of the biodegradable polymer is gradually proceeds immediately after the application thereof to fields to decompose and deteriorate the film, the strength of the film is reduced during the process, and the water in the fields rapidly penetrates into the coated granule through the film after the lapse of a predetermined period of time, resulting in the release of the active ingredient of the coated granule. Moreover, the biodegradable polymer likewise serves to easily break the coating film made of the thermoplastic resin remaining after the complete release of the active ingredient into pieces to thus improve the decomposition speed of the film, i.e., the rate of film-decomposition or disappearance.

In the present invention, the biodegradable polymer hardly soluble or insoluble in water is not restricted to specific ones inasmuch as they can gradually be decomposed under natural environmental conditions, but is preferably an ester of a hydroxycarboxylic acid such as an aliphatic polyester represented by the following general formula (I):

$$H-(O-R_1-O-CO-R_2-CO)_n-O-R_1-OH \quad (I)$$

treating a polyamino acid solution obtained by reacting an acid anhydride with an amine and/or a diamine at a temperature ranging from 100 to 200° C., preferably 110 to 160° C. to remove the solvent and then pulverizing the solid product in a ball mill or a mixer. The heat treatment may be carried out at a lower temperature so far as the solvent can be removed, but most of solvents in which thermosetting resins are soluble are in general polar ones and frequently have a high boiling point of not less than 100° C.

The thermosetting resins in a powdery state preferably have a particle size ranging from 0.1 to 100 μm and the amount thereof to be added to the film preferably ranges from 0.1 to 30% by weight on the basis of the total weight of the film.

The particulate coated pesticide according to the present invention may comprise, in the coating film, a biodegradable polymer hardly soluble or insoluble in water in order to control the film-disintegration time of the film. The biodegradable polymer hardly soluble or insoluble in water shows an effect of reducing the film-disintegration time of the resulting film.

The backbone chain of the biodegradable polymer hardly soluble or insoluble in water used in the present invention is cleaved by the action of metabolites of microorganisms in soil, in particular, hydrolases or other hydrolases, for example, introduced into soil from air or water or artificially mixed with soil. The biodegradable polymer may further be hydrolyzed under the usual environmental (wherein $R_1$ and $R_2$ each independently represents an alkylene group having 2 to 10 carbon atoms and n is a numerical value ranging from 10 to 2000).

Specific examples of the polymeric hydroxycarboxylic acids represented by formula (I) are polylactones such as poly-$\epsilon$-caprolactone, poly-$\delta$-valerolactone, poly-$\beta$-propiolactone, poly-$\gamma$-butyrolactone, polylactic acid and polyglycolic acid; polyhydroxy alkanoates such as poly-3-hydroxybutyric acid and poly-3-hydroxyvaleric acid; polyacid anhydrides, polyorthoesters, urethane bond-containing aliphatic polyesters and copolymers thereof. These biodegradable polymer hardly soluble or insoluble in water may be combined with any thermoplastic substance. The molecular weight of such a thermoplastic substance preferably ranges from about 2000 to about 300,000. The polylactic acid monomer may be present in any kinds of three optical isomers, i.e., L-, D- and D, L-isomers, and all of these isomers may ensure the intended purpose of the present invention.

The amount of the biodegradable polymer hardly soluble or insoluble in water to be added to the coating film preferably in the range of from 0.1 to 30% by weight on the basis of the total weight of the film.

The coated granular pesticide according to the present invention may be produced by spraying a granular pesticide which is in the fluidized state by the action of a hot gas flow with a mixed solution obtained by dissolving film-forming materials in a solvent while drying and removing the solvent sprayed on the pesticide to thus form a film on the surface of the granular pesticide.

An example of a preferred coating device usable in the method for producing the coated granular pesticide according to the present invention is shown in FIG. 2.

In FIG. 2, a granular pesticide (5) is fed to a spouting column (1) through an opening (2) for introducing granular pesticides disposed on the side of the column. A fluid gas, preferably air which is introduced into the device by a blower (10), passes through an orifice flowmeter (9) and is heated in a heat exchanger (8), upwardly passes through the spouting column (1) and is discharged through an outlet for exhaust gas (3) disposed on the upper portion of the spouting column (1). The heating of the fluid gas can be carried out using, for instance, steam (SL). The hot fluid gas having a temperature of $T_1$ heats the granular pesticide (5) up to a temperature of $T_2$, while maintaining the fluidized state of the granular pesticide. On the other hand, a thermoplastic resin as a film-forming material is dissolved in an organic solvent in a dissolution tank (11) while applying heat thereto using, for instance, steam (SL) and optionally other additives are dissolved or mixed with the solution. The resulting mixed solution (12) of the film-forming materials is sprayed on the granular pesticide (5) flowing through the spouting column (1), through a pump (6) and a spray nozzle (4), thus the mixed solution (12) of the film-forming materials is adhered to the surface of the granular pesticide simultaneous with or in parallel with the evaporation of the solvent present in the mixed solution (12) through heating to thus form a film on the granular pesticide (5). The solvent thus evaporated is discharged through the outlet for exhaust gas (3) together with the fluid gas. They can be separated from one another and can be recovered by the usual method. The operation of this device can be optimized by appropriately adjusting, for instance, the flow rate and the temperature $T_1$ of the fluid gas, the temperature $T_2$ of the granular pesticide (5) and the temperature $T_3$ of the exhaust gas depending on the characteristic properties (for instance, particle size) of the granular pesticide (5), the composition of the mixed solution (12) of the film-forming materials or the like. The completed granular pesticide is removed from the device through an opening (7) for withdrawal fitted to the lower end of the spouting column (1).

In the present invention, it is possible to use a mixture of at least two coated granular pesticides which have a different release-suppression term of the active ingredient from one another. Such a mixture is particularly useful since the release-suppression term and the released amount of the active ingredient having insecticidal, fungicidal or herbicidal effect required for the cultivation and management of field crops and garden crops can be controlled or adjusted by a single application thereof.

When using an active ingredient having insecticidal and/or fungicidal effects as the hardly water-soluble active ingredient, the combination of a plurality of coated granular pesticides having different release-suppression terms is not limited to specific ones inasmuch as any specific combination permits the long-lasting release of the active ingredient having insecticidal and/or fungicidal effects required for the cultivation and management of field crops over the entire growing period, but it is preferred to appropriately combine an early release-intiation type coated granular pesticide which can initiate the release of the active ingredient after 2 to 5 weeks from the application thereof to fields and a late release-intiation type one which can initiate the release of the active ingredient after 6 to 9 weeks from the application thereof to fields.

Such a combination of the early release-intiation type coated granular pesticide with the late release-intiation type one is suitably used for controlling blast of paddy rice (for controlling leaf blast which would be developed after one month from the rice transplanting and head blast which would be developed after 2.5 months from the rice transplanting).

When using an active ingredient having a herbicidal effect as the hardly water-soluble active ingredient, the combination of a plurality of coated granular pesticides having different release-suppression terms is not limited to specific ones inasmuch as any specific combination permits the long-lasting release of the active ingredient having a herbicidal effect required for the cultivation and management of field crops over the entire growing period, but it is preferred to appropriately combine an early release-intiation type coated granular pesticide which can initiate the release of the active ingredient after 1 to 14 days from the application thereof to fields and a late release-intiation type one which can initiate the release of the active ingredient after 15 to 40 days from the application thereof to fields.

The coated granular pesticide of the present invention permits the initiation of the release of the hardly water-soluble active ingredient at the time when crops require the active ingredient. Therefore, the pesticide of the present invention does not cause any chemical injury of crops and also permits the sustained release of the active ingredient at a low concentration which does not adversely affect the growing environment of the crops.

For this reason, even if the coated granular pesticide is applied to fields simultaneously with the transplantation of seedlings, the granular pesticide initiates the release of its hardly water-soluble active ingredient after the rooting of the transplanted seedlings and the released hardly water-soluble active ingredient is completely consumed for weed-killing, pasteurization and for controlling insects. Accordingly, the transplanted seedlings are not adversely affected by the pesticide and the production of field crops with safety is permitted.

It is optionally possible to use a coated granular pesticide comprising a coated water-soluble active ingredient in combination with the pesticide of the present invention, in such an extent that the initial release thereof does not have any adverse influence. In this case, the release-initiation time corresponds to the time when cracks are formed on the film.

In the present invention, the coated granular pesticide and a mixture thereof may be applied to fields at any desired period, but they are preferably applied simultaneously with or immediately before the transplantation of seedlings since the time required for farm working can substantially be reduced. Particularly preferably, they are applied to holes or furrow formed on the side of seedlings simultaneously with transplantation of seedlings, or alternatively they are applied to a substrate for raising seedlings immediately before the transplantation thereof and immediately thereafter, the seedlings are transplanted to fields. It is also possible to combine the coated granular pesticide according to the present invention or a mixture thereof with a commercially available pesticide and to apply the resulting mixture so that the latter would be released during the controlled release term of the pesticide of the present invention.

The coated granular pesticide of the present invention can likewise be incorporated into a seedling-support substance having water holding properties (hereinafter referred to as "water-holding material") and used as a substrate for raising seedlings. Such a substrate for raising seedlings consisting of the coated granular pesticide and the water-holding material is suitably used in the cultivating method which comprises seeding rice seeds in a nursery box, raising the seedlings and then transplanting the resulting seedlings to fields. The use of the substrate for raising seedlings according to the present invention can eliminate the application of any granular pesticide having an insecticidal, fungicidal or herbicidal effect prior to transplantation of seedlings and this accordingly permits the substantial reduction in the quantity of work during transplantation, in particular, that of a large-scale farm household who raises seedlings using a large number of nursery boxes. In addition, if raising seedlings by the use of the substrate for raising seedlings according to the present invention, the seedlings are transplanted while the coated granular pesticide is held around the rooting of the seedlings and therefore, this leads to improvement in the absorption and utilization efficiency of the active ingredient released from the coated granular pesticide, substantial reduction of the active ingredient washed away into the soil and reduction of environmental loads.

The water-holding materials usable herein are not restricted to any specific one inasmuch as they have good water holding properties and examples thereof are natural soil, naturally occurring organic substances such as wood chips, scum of pulp, peat-moss, sphagnum and coir; foamed resins; and inorganic porous materials such as perlite and vermiculite, but preferred are vermiculite, peat-moss and coconut meal because they are inexpensive and stable supply thereof can be ensured. These water-holding materials may be used alone or in a blend of at least two of them. In addition, these water-holding substances may further comprise various kinds of additives for controlling physico-chemical properties such as pH and electrical conductivity (EC).

To the substrate for raising seedlings according to the present invention, there may, if needed, be added fertilizers. In this respect, however, if using fast-acting fertilizers, they are preferably used in amounts of about 1 to 4 g, respectively, as expressed in terms of N (nitrogen), $P_2O_3$ (phosphoric acid) and $K_2O$ (potash) per unit nursery box (internal size: 28 cm (length)×58 cm (width)×3 cm (depth). If these fertilizer components each exceeds 4 g, young seedlings may suffer from concentration injury.

To the substrate for raising seedlings according to the present invention, there may be applied, in addition to fast-acting fertilizers, coated granular fertilizer whose release rate is physically controlled by coating each granular fertilizer with a film and micro elements.

Examples of such micro elements are compounds of, for instance, magnesium, calcium, iron, manganese, boron, zinc, copper and molybdenum.

Water-soluble micro elements are fast-acting fertilizers and therefore, they are effective for soil deficient in these component, but have such a tendency that they are washed away if the amount of water used for irrigation increases. Moreover, if the added amount of the micro elements is large, seedlings are damaged due to their excess and for this reason, the use of micro elements soluble in citric acid is recommended. Such citric acid-soluble micro elements are hardly soluble in water and the elements thereof are slowly released even if they are added to the substrate in a large amount during raising seedlings, and therefore, the use of such micro elements are particularly preferred in order to prevent any deficiency of these trace elements during raising seedlings.

Examples of the foregoing coated granular fertilizers are those disclosed in JP-A 56567/1994 or JP-A 4887/1993 in which an oil modified alkyd resins is used as a coating film; and those disclosed in JP-A 147888/1988 wherein a polyolefinic resin is used as such a coating film and specific examples thereof usable herein include coated granular fertilizers commercially available under the trade names of Long (Asahi Chemical Industry Co., Ltd.), LP Coat (Chisso Corporation), Celacoat (Central Glass Co., Ltd.) and M Coat (Mitsubishi Chemical Co.). If these fertilizers are used for raising seedlings, roots of seedlings are formed around the granular fertilizer and thus the fertilizer-absorption and -utilization efficiencies are markedly improved.

The coated granular fertilizer preferably has a release rate during the seedling-raising term ranging from 0.5 to 10% and more preferably 1 to 7%. Fertilizers having a release rate beyond the range defined above may also be used, but if the release rate exceeds 10%, seedlings may suffer from concentration injury due to the fertilizer component, while if it is less than 0.5%, the seedlings may insufficiently grow. Moreover, it is necessary to adjust the amount of the fertilizer to be applied depending on the term for raising seedlings to be transplanted.

These coated granular fertilizers may be mixed with the water-holding materials in such an amount that does not impair the functions of the water-holding materials (water-holding and seedling-supporting functions). More specifically, if the amount of the coated granular fertilizer is excessively large, the water-holding properties of the resulting substrate are impaired, while if it is extremely small, sufficient fertilization during raising seedling cannot be ensured. Accordingly, it is preferable to admix 5 to 50 parts by weight of the coated granular fertilizer with 50 to 95 parts by weight of the water-holding material. These numerical values defined above correspond to cases where the water-holding material is assumed to be a mineral substance such as natural soil. In case of, for instance, water-holding materials having a smaller specific gravity such as vermiculite and peat-moss, however, the amount thereof to be used may be less than 50 parts by weight so far as the resulting mixture exhibits functions of water-holding materials. Therefore, the foregoing range is simply a standard for judgment.

The amount of the coated granular pesticide to be used varies depending on the content of the active ingredient thereof, but it is in general sufficient to use the same in a small amount and thus the pesticide does not impair the functions of the water-holding material. The amount of the coated pesticide as a standard is preferably not more than 100 g per nursery box having the size specified above.

Moreover, the substrate for raising seedling according to the present invention may likewise comprise a further component such as a growth regulator, a growth promoter or the like.

The substrate for raising seedling according to the present invention may be prepared by any conventionally known method. For instance, it can be prepared by admixing a water-holding material and the coated granular pesticide as well as optional components such as a fertilizer and micro elements in a mixing machine. The resulting mixture (the substrate for raising seedling according to the present invention) may be used in a variety of methods. For instance, it may be used as bed soil and/or soil cover in fields or nursery boxes; or it may be mixed with seeds upon seeding. In particular, when it is used in a nursery box, it can be recommended that a layer of a mixture of seeds with the substrate for raising seedling according to the present invention, which comprises a water-holding material, the coated granular pesticide and coated granular fertilizers, should be arranged between a bed soil layer and a soil cover layer. This is because the active ingredient, fertilizer components and micro elements are present in the vicinity of seeds and therefore, these components are absorbed through roots and used with a high efficiency, after rooting the seeds.

The present invention will hereinafter be described in more detail with reference to the following Production Experiments of Granular Pesticides and Production Experiments and Examples, but the present invention is not limited to these specific Examples. In the following Examples, the term "%" means "% by weight" unless otherwise specified.

Production of Granular Pesicide
Granular Pesticides (G.P.) A to M

Each mixture of ingredients for granules having each corresponding composition shown in Table 1 was kneaded in a kneader while adding water, followed by granulation through extrusion and forming into spherical granules using a shaping machine. Then the granulated product was dried to thus give each granular pesticide containing a hardly water-soluble active ingredient and having a particle size ranging from 0.8 to 1.4 mm. In the foregoing preparation, the polymer used for preparing the granular pesticide D was used after dissolving in water.

TABLE 1

Composition of G.P. (% by weight)

| G.P. | Active Ingredient | | Material I | | Material II | | Material III | |
|---|---|---|---|---|---|---|---|---|
| A | A.M.[1] A | 10 | bentonite | 50 | clay | 40 | | |
| B | A.M. A | 5 | bentonite | 95 | | | | |
| C | A.M. B | 20 | bentonite | 40 | starch | 20 | clay | 20 |
| D | A.M. C | 5 | bentonite | 5 | kaolin | 85 | polymer | 5 |
| E | A.M. D | 2 | starch | 95 | gelatin | 1 | ammonium phosphate | 2 |
| F | A.M. A | 15 | bentonite | 60 | clay | 25 | | |
| G | A.M. A | 15 | bentonite | 30 | clay | 55 | | |
| H | A.M. E | 7 | bentonite | 30 | clay | 63 | | |
| I | A.M. F | 10 | bentonite | 30 | clay | 60 | | |
| J | A.M. E | 7 | bentonite | 30 | clay | 53 | | |
|   | A.M. F | 10 | | | | | | |
| K | A.M. A | 14.5 | bentonite | 30 | clay | 55.5 | | |
| L | A.M. C | 3.5 | bentonite | 30 | clay | 66.5 | | |
| M | A.M. C | 1 | bentonite | 30 | clay | 69 | | |

1) A.I.=Active Ingredient.

*: Active Incrredient:
  A.I. A: 2-benzothiazol-2-yloxy-N-methylacetoanilide (content=87%)
  A.I. B: 2-chloro-4-ethylamino-6-isopropylamino-s-triazine (content=75%)
  A.I. C: 1-(6-chloro-3-pyridylmethyl)-N-nitroimidazolidin-2-ylideneamine (content=71%)
  A.I. D: 2-chloro-4,6-bis(ethylamino)-s-triazine (content=50%)
  A.I. E: 5-methyl-1,2,4-triazolo(3,4-b)benzothiazole (content=75%)
  A.I. F: 1,3-bis(carbamoylthio)-2-(N,N-dimethylamino) propane hydrochloride (content=50% by weight)

*: Water-Swelling Material
  Bentonite: a product available from Wako Pure Chemical Industry Co., Ltd.
  Starch: corn starch available from Wako Pure Chemnical Industry Co., Ltd.
  Gelatin

*: Binder, Auxiliary Agent for Granulation or the Like
  Polymer: sodium polyacrylate (degree of polymerization: 15 22,000 to 70,000)
  Ammonium Phosphate: diammonium phosphate
  Clay
  Kaolin Synthesis of Thermosetting Resin To a 300 ml four-necked flask, there was added 100 ml of diethylene glycol dimethyl ether, followed by dissolution of 18.9 g of α, ω-bis(3-aminopropyl)polydimethyl siloxane, cooling the content of the flask down to a temperature of 10° C. while stirring with a stirring machine, subsequent addition of 4.6 g of maleic anhydride and reaction of these ingredients to give a thermosetting resin A.

In the same manner, to a 300 ml four-necked flask, there was added 100 ml of N,N-dimethylacetamide, followed by dissolution of 4.7 g of p-aminobenzoic acid, cooling the content of the flask down to a temperature of 7° C. while stirring with a stirring machine, subsequent addition of 18.9 g of benzophenone tetracarboxylic acid dianhydride and reaction of these ingredients to give a thermosetting resin B.

Production of Coated Granular Pesticide (C.G.P.)

As has been shown in FIG. 2, hot air having a high temperature was passed through the interior of a spouting column (1) which was in a shape having a column diameter of 250 mm, a height of 2000 mm, an air jet-outlet diameter of 50 mm and an angle at the conical part of 50 degrees, from its bottom to the top, i.e., upwardly passed through the column. A blower (10) was used to introduce air, through an orifice flowmeter (9), into a heat exchanger (8) in which the air was heated to a desired high temperature and was then guided to the spouting column (1) and finally discharged through an outlet (3) for exhaust gas which was positioned at the upper portion of the spouting column (1). Then there was introduced 10 kg of each granular pesticide (5) listed in Tables 2 to 7 (provided that 3 kg of each pesticide was introduced when producing coated granular pesticides 33 to 46) into the interior of the spouting column (1) through which the hot air was circulated, through an opening (2) for introducing granules positioned on the side of the spouting column (1) to thus fluidize the granular pesticide (5) in the powdery state. In this regard, the flow rate and temperature of the hot air were appropriately controlled depending on the kinds of samples. The flow rate of the granule (5) was controlled while monitoring the same by the orifice flowmeter and the temperature thereof was adjusted while monitoring the hot air temperature ($T_1$), the granule temperature ($T_2$) and the exhaust gas temperature ($T_3$). The production of each coated granular pesticide was carried out at a flow rate as determined by flowmeter (9) of 4 m³/min and the hot air temperature ($T_1$) of 100° C.±2° C. (provided that $T_1$ was set at 80° C.±2° C. when producing coated granular pesticides 33 to 40).

On the other hand, there were introduced, into a dissolution bath (11), ingredients for films listed in Tables 2 to 7 and tetrachloroethylene as a solvent (provided that toluene was used when producing coated granular pesticides 33 to 40), followed by admixing and stirring these components to give a 2.5% solution (12) of film-forming materials (provided that a 5.0% solution of film-forming materials was used when producing coated granular pesticides 41 to 46, 49 and 50). In the foregoing preparation, the thermosetting resins in liquid states were used as such, while those in powdery states were pulverized in a ball mill, then classified using a sieve having a pore size of 75 μm and particles which could pass through the sieve were used.

The solution (12) was fed to a spray nozzle (4), which was a full cone type hydraulic nozzle having a diameter of 0.6 mm and positioned at a lower portion of the spouting column (1), by the action of a pump (6), at a flow rate of 0.3 kg/min (provided that it was set at 0.2 kg/min when producing coated granular pesticides 33 to 40), then injected toward and sprayed on the granular pesticide (5) in a fluidized condition.

Such a spraying operation was initiated when the temperature ($T_2$) of the granular pesticide (G.P.) which was in the fluidized state reached a given level, and the operation was continued for a given period of time, followed by drying the product for a predetermined time. After the drying was completed, the blower (10) was stopped and the coated granular pesticide (5) was discharged through an opening (7) for withdrawal positioned at the lowest portion of the spouting column (1) to thus obtain each coated granular pesticide (C.G.P.) 1 to 55 having a covering ratio listed in the following Table 2 to Table 7.

TABLE 2

| C.G.P. | Resin 1 | | Resin 2 | | Resin 3 | | Filler | | S.A.A. | | G.P. | Coating Ratio (%) |
|---|---|---|---|---|---|---|---|---|---|---|---|---|
| 1 | PE-1 | 40 | | | | | talc | 60 | Nonion | 10 | A | 15 |
| 2 | PE-1 | 20 | | | | | talc | 80 | Nonion | 5 | A | 15 |
| 3 | PE-1 | 20 | | | | | talc | 80 | Nonion | 3 | A | 15 |
| 4 | PE-1 | 20 | | | | | talc | 80 | Nonion | 2 | A | 15 |
| 5 | PE-1 | 20 | | | | | talc | 80 | Nonion | 1 | A | 15 |
| 6 | PE-1 | 20 | | | | | talc | 80 | Nonion | 0.5 | A | 15 |
| 7 | PE-2 | 28 | EVA | 2 | | | clay | 70 | | | B | 20 |
| 8 | PE-2 | 69 | WAX | 30 | PCL | 1 | | | | | C | 20 |
| 9 | PE-2 | 5 | | | | | talc | 95 | | | C | 15 |
| 10 | PP-1 | 30 | PCL | 5 | | | CaCO$_3$ | 65 | | | D | 20 |
| 11 | PP-1 | 20 | | | | | | | clay | 80 | Nonion | 0.1 | E | 15 |
| 12 | WAX | 70 | | | | | talc | 30 | | | E | 25 |

*: The amount of the surfactant (S.A.A.) is expressed in terms of % by weight on the basis of the total weight of the Resin 1, Resin 2, Resin 3 and Filler (which is 100% by weight).

TABLE 3

| C.G.P. | Resin 1 | | Resin 2 | Filler 1 | | Filler 2 | | S.A.A. | G.P. | Coating Ratio (%) |
|---|---|---|---|---|---|---|---|---|---|---|
| 13 | PE-3 | 10 | | IB | 1 | talc | 89 | | F | 20 |
| 14 | PE-3 | 20 | | IB | 1 | talc | 79 | | F | 20 |
| 15 | PE-3 | 30 | | IB | 1 | talc | 69 | | F | 20 |
| 16 | PE-3 | 20 | | MC | 3 | talc | 77 | | F | 20 |

TABLE 3-continued

| C.G.P. | Resin 1 | | Resin 2 | | Filler 1 | | Filler 2 | | S.A.A. | | G.P. | Coating Ratio (%) |
|---|---|---|---|---|---|---|---|---|---|---|---|---|
| 17 | PE-3 | 10 | PE-4 | 10 | MC | 5 | talc | 75 | | | F | 20 |
| 18 | PE-3 | 10 | PE-4 | 10 | HPC | 3 | talc | 67 | | | F | 20 |
| 19 | PE-2 | 20 | | | IB | 1 | talc | 79 | Nonion | 0.5 | F | 20 |
| 20 | PE-2 | 20 | | | MC | 10 | talc | 70 | | | F | 20 |
| 21 | PE-2 | 20 | | | HPC | 1 | talc | 79 | | | F | 15 |
| 22 | PE-2 | 20 | | | HPC | 5 | talc | 75 | | | F | 15 |

*: The amount of the surfactant (S.A.A.) is expressed in terms of % by weight on the basis of the total weight of the Resin 1, Resin 2, Filler 1 and Filler 2 (which is 100% weight).

TABLE 4

| C.G.P. | Resin 1 | | Resin 2 | | Thermosetting Resin | | Filler | | S.A.A. | | G.P. | Coating Ratio (%) |
|---|---|---|---|---|---|---|---|---|---|---|---|---|
| 23 | PE-3 | 10 | | | Solution 1 | 1 | talc | 89 | | | F | 20 |
| 24 | PE-3 | 20 | | | Solution 1 | 1 | talc | 79 | | | F | 20 |
| 25 | PE-3 | 30 | | | Solution 1 | 1 | talc | 69 | | | F | 20 |
| 26 | PE-3 | 10 | PE-2 | 10 | Solution 2 | 2 | talc | 78 | | | F | 20 |
| 27 | PE-2 | 10 | | | Powder 1 | 5 | talc | 85 | | | F | 20 |
| 28 | PE-2 | 20 | PP-2 | 10 | Powder 1 | 3 | talc | 77 | | | F | 20 |
| 29 | PE-2 | 20 | | | Powder 1 | 1 | talc | 69 | Nonion | 0.5 | F | 20 |
| 30 | PP-2 | 35 | | | Solution 2 | 10 | talc | 55 | | | F | 20 |
| 31 | PP-2 | 20 | | | Powder 2 | 1 | talc | 79 | | | F | 15 |
| 32 | PP-2 | 20 | | | Powder 2 | 5 | talc | 75 | | | F | 15 |

*: The amount of the surfactant (S.A.A.) is expressed in terms of % by weight on the basis of the total weight of the Resin 1, Resin 2, Thermosetting Resin and Filler (which is 100% by weight).

TABLE 5

| C.G.P. | Resin 1 | | Resin 2 | | Filler | | G.P. | Coating Ratio (%) |
|---|---|---|---|---|---|---|---|---|
| 33 | PE-3 | 20 | EVA | 20 | talc | 60 | G | 20 |
| 34 | PE-2 | 18 | Water-sol. | 2 | talc | 80 | G | 20 |
| 35 | Biodegrad. 1 | 1 | PE-2 | 19 | talc | 80 | G | 20 |
| 36 | Biodegrad. 1 | 3 | PE-2 | 17 | talc | 80 | G | 20 |
| 37 | Biodegrad. 1 | 10 | PE-2 | 30 | talc | 60 | G | 20 |
| 38 | Biodegrad. 2 | 5 | PE-2 | 15 | talc | 80 | G | 20 |
| 39 | Biodegrad. 3 | 2 | PE-2 | 18 | talc | 80 | G | 20 |
| 40 | Biodegrad. 4 | 10 | PE-2 | 20 | talc | 70 | G | 20 |

TABLE 6

| C.G.P. | Resin 1 | | Resin 2 | | Filler | | G.P. | Coating Ratio (%) |
|---|---|---|---|---|---|---|---|---|
| 41 | PE-2 | 20 | paraffin | 2 | talc | 80 | H | 20 |
| 42 | PE-2 | 18 | paraffin | 2 | talc | 80 | H | 20 |
| 43 | PE-2 | 18 | paraffin | 2 | talc | 80 | I | 20 |
| 44 | PE-2 | 15 | paraffin | 5 | talc | 80 | I | 20 |
| 45 | PE-2 | 18 | paraffin | 2 | talc | 80 | J | 20 |
| 46 | PE-2 | 15 | paraffin | 5 | talc | 80 | J | 20 |
| 47 | PE-2 | 18 | | | talc | 82 | K | 20 |
| 48 | PE-2 | 18 | | | talc | 82 | L | 20 |
| 49 | PE-2 | 15 | | | talc | 85 | L | 20 |
| 50 | PE-2 | 15 | WAX 2 | 5 | talc | 80 | M | 20 |

TABLE 7

| C.G.P. | Resin 1 | | Resin 2 | | Filler 1 | | Filler 2 | | S.A.A. | | G.P. | Coating Ratio (%) |
|---|---|---|---|---|---|---|---|---|---|---|---|---|
| 51 | PE-2 | 15 | | | talc | 85 | | | Nonion | 1 | F | 20 |
| 52 | PE-2 | 25 | | | talc | 75 | | | Nonion | 2 | F | 20 |
| 53 | PE-2 | 30 | | | talc | 70 | | | Nonion | 1 | F | 20 |
| 54 | PE-2 | 10 | PE-3 | 20 | talc | 67 | HPC | 3 | | | F | 20 |
| 55 | PE-3 | 10 | | | talc | 89 | Powder 1 | 1 | | | F | 20 |

*: The amount of the surfactant (S.A.A.) is expressed in terms of % by weight on the basis of the total weight of the Resin 1, Resin 2, Filler 1 and Filler 2 (which is 100% by weight).
PE-1: low density polyethylene: MI=20; d=0.922 g/cmn$^3$
PE-2: ethylene-carbon monoxide copolymer: MI=0.75; CO=0.95% by weight
PE-3: low density polyethylene: MI=23; d=0.916 g/cm$^3$
PE-4: low density polyethylene: MI=70; d=0.915 g/cm$^3$
PP-1: copolymer type atactic polypropylene having an ethylene content of 3%: Mw=60,000
PP-2: polypropylene: Mw=10,000; d=0.9 g/cm$^3$
EVA: ethylene-vinyl acetate copolymer: MI=20; vinyl acetate content=30% by weight
WAX: polyethylene wax: Mn=8,000; d=0.97 g/cm$^3$
WAX 2: polyethylene wax: Mn=2,000; d=0.92 g/cm$^3$
paraffin: mp=68 to 70° C.
PCL: poly-$\epsilon$-caprolactone: Mw=50,000
IB: isobutylene type copolymer
MC: methyl cellulose
Biodegrad. 1: 1,4-butanediol-succinic acid co-polycondensate: Mn=59,000
Biodegrad. 2: poly-L-lactic acid: Mw=60,000
Biodegrad. 3: polycaprolactone: Mw=50,000
Biodegrad. 4: 3-hydroxybutyric acid/3-hydroxyvaleric acid copolymer: Mw=150,000, 3-hydroxyvaleric acid content=20 mole %
Water-Sol.: polyethylene oxide: Mw=150,000 to 400,000
HPC: hydroxypropyl cellulose: 150 to 400 cp
Nonion: hexaoxyethylene nonyl phenyl ether: HLB=13
talc: average particle size=5 $\mu$m
CaCO$_3$: calcium carbonate having an average particle size of 5 $\mu$m
clay: average particle size=5 $\mu$m
Solution 1: thermosetting resin A
Solution 2: thermosetting resin B
Powder 1: thermosetting resin A
Powder 2: thermosetting resin B
Production of Coated Granular Pesticide Mixture The coated granular pesticides (C.G.P.) 41 to 46 (Table 6) produced in the foregoing Production Experiments were blended in the rates specified below and each blend was uniformly stirred in a kneader to give various coated granular pesticide mixtures (coated granular pesticide mixtures 1 to 16).
C.G.P. Mixture 1:
  (C.G.P. 41: C.G.P. 42=1:1)
C.G.P. Mixture 2:
  (C.G.P. 41: C.G.P. 42=2:1)
C.G.P. Mixture 3:
  (C.G.P. 41: C.G.P. 42 1:2)
C.G.P. Mixture 4:
  (C.G.P. 43: C.G.P. 44=1:1)
C.G.P. Mixture 5:
  (C.G.P. 43: C.G.P. 44=2:1)
C.G.P. Mixture 6:
  (C.G.P. 43: C.G.P. 44=1:2)
C.G.P. Mixture 7:
  (C.G.P. 41: C.G.P. 43=1:1)
C.G.P. Mixture 8:
  (C.G.P. 42: C.G.P. 44=1:1)
C.G.P. Mixture 9:
  (C.G.P. 42: C.G.P. 45=1:1)
C.G.P. Mixture 10:
  (C.G.P. 41: C.G.P. 46=1:1)
C.G.P. Mixture 11:
  (C.G.P. 51: C.G.P. 53=1:1)
C.G.P. Mixture 12:
  (C.G.P. 51: C.G.P. 53=7:3)
C.G.P. Mixture 13:
  (C.G.P. 51: C.G.P. 53=6:4)
C.G.P. Mixture 14:
  (C.G.P. 51: C.G.P. 52: C.G.P. 53=60:25:15)
C.G.P. Mixture 15:
  (C.G.P. 53: C.G.P. 55=1:9)
C.G.P. Mixture 16:
  (C.G.P. 53: C.G.P. 54: C.G.P. 55=15:15:70)
Release-Confirmation Test Release-confirmation tests were carried out using coated granular pesticides 1 to 12 (Table 2) produced in the foregoing experiments for the production of these granules. In these tests, there was determined the period required for the formation of cracks on the pesticides, the breakage of the films thereof and the outward release of the granular pesticides present therein (release-suppression term), according to the following manner.

To a beaker, there were added 500 ml of distilled water and 0.1 g of each coated granular pesticide 1 to 12, followed by the inspection of the coated granular pesticide for film-disintegration behavior with period. In addition, the distilled water in the beaker was sampled at regular intervals, the hardly water-soluble active ingredient present in the sampled distilled water was analyzed by high performance liquid chromatography to thus determine the priod required till the release of the active ingredient was detected and the period thus determined was defined to be the release-suppression term of the granular pesticide. The temperature of the distilled water was maintained at 20° C. and the determination was carried out for 30 days after the addition of the granule to distilled water. The results thus obtained are summarized in Table 8.

TABLE 8

| Sample | | Release-Suppression Term (day) |
|---|---|---|
| Example 1 | C.G.P. 1 | 10 |
| Example 2 | C.G.P. 2 | 6 hrs. |
| Example 3 | C.G.P. 3 | 0.5 |
| Example 4 | C.G.P. 4 | 1.0 |
| Example 5 | C.G.P. 5 | 1.5 |
| Example 6 | C.G.P. 6 | 5 |
| Example 7 | C.G.P. 7 | 15 |
| Example 8 | C.G.P. 8 | 24 |
| Example 9 | C.G.P. 9 | 0.5 |
| Example 10 | C.G.P. 10 | 17 |
| Example 11 | C.G.P. 11 | 10 |
| Example 12 | C.G.P. 12 | 20 |

The disintegration process of the coated granular pesticide 2 is shown in FIG. 3. FIGS. 3A, 3B and 3C are photographs taken at 6 hours, 6 hours and 5 minutes, and 6 hours and 10 minutes after the coated granular pesticide 2 was introduced into a beaker, respectively.

As will be seen from the photographs shown in FIGS. 3A to 3C, it takes a constant time period till cracks are formed on the film of this coated granular pesticide and any hardly water-soluble active ingredient is not released at all before the formation of the cracks, but if once such cracks are formed, the disintegration of the film proceeds acceleratedly and the granular pesticide present therein is rapidly released.

Moreover, the results observed for the coated granular pesticides 2 to 6 which differ from one another in the added amount of the surfactant indicate that the larger the amount of the surfactant added, the shorter the release-suppression term and that the addition of a surfactant is effective for the control of the release-suppression term.

Test 1 for Release in Water

Tests for release in water were carried out using the coated granular pesticides 13 to 32 (Tables 3 and 4) produced in the foregoing Production Experiments. To a beaker, there were added 1000 ml of distilled water and 0.1 g of each coated granular pesticide (C.G.P.), followed by the inspection of the coated granular pesticide for film-disintegration behavior with term. In addition, the distilled water in the beaker was sampled at regular intervals, the hardly water-soluble active ingredient present in the sampled distilled water was analyzed by high performance liquid chromatography. The temperature of the distilled water was maintained at 25° C. during the test and the determination was carried out for 28 days after the addition of the granule to distilled water. The results thus obtained are summarized in Tables 9 and 10. In Comparative Example 1, the foregoing granular pesticide F free of coating film was used.

TABLE 9

| | | Concn. of Active Ingredient in Water (ppm) | | | | |
|---|---|---|---|---|---|---|
| | Sample | day 1 | day 3 | day 7 | day 14 | day 28 |
| Ex. 13 | C.G.P. 13 | 0.0 | 0.3 | 0.8 | 1.2 | 1.6 |
| Ex. 14 | C.G.P. 14 | 0.0 | 0.0 | 0.3 | 0.8 | 1.5 |
| Ex. 15 | C.G.P. 15 | 0.0 | 0.0 | 0.0 | 0.1 | 1.0 |
| Ex. 16 | C.G.P. 16 | 0.0 | 0.0 | 0.0 | 0.6 | 1.3 |
| Ex. 17 | C.G.P. 17 | 0.0 | 0.0 | 0.0 | 0.8 | 1.8 |
| Ex. 18 | C.G.P. 18 | 0.0 | 0.0 | 0.0 | 0.0 | 0.7 |
| Ex. 19 | C.G.P. 19 | 0.0 | 1.0 | 1.6 | 2.0 | 2.5 |
| Ex. 20 | C.G.P. 20 | 0.0 | 0.0 | 0.4 | 1.0 | 2.0 |
| Ex. 21 | C.G.P. 21 | 0.0 | 0.0 | 0.0 | 0.7 | 1.4 |

TABLE 9-continued

| | | Concn. of Active Ingredient in Water (ppm) | | | | |
|---|---|---|---|---|---|---|
| | Sample | day 1 | day 3 | day 7 | day 14 | day 28 |
| Ex. 22 | C.G.P. 22 | 0.0 | 0.0 | 0.1 | 0.9 | 1.8 |
| Comp. Ex. 1 | G.P. F | 0.8 | 1.2 | 2.5 | 2.9 | 3.0 |

The results listed in Table 9 indicate that the granules of Comparative Example 1 initiates the release of the active ingredient immediately after the introduction thereof into water, whereas for C.G.P. Nos. 13 to 22 according to the present invention, which comprise water-absorbing polymer fine particles and/or water-soluble polymer fine particles, any active ingredient is not detected, on day 1 after the introduction, clearly showing that the release of the active ingredient is initially inhibited and the active ingredient certainly undergoes sustained release in the samples of the present invention.

Moreover, the results observed for C.G.P. Nos. 13 to which differ from one another in the amount of Resin 1 included in the water-absorbing polymer fine particles and/ or the water-soluble polymer fine particles with respect to the isobutylene type copolymer (Table 3) also indicate that the larger the amount of Resin 1, the later the release-suppression term of the active ingredient and that the control of the amount of Resin 1 would be effective for the adjustment of the release-suppression term.

TABLE 10

| | | Concn. of Active Ingredient in Water (ppm) | | | | |
|---|---|---|---|---|---|---|
| | Sample | day 1 | day 3 | day 7 | day 14 | day 28 |
| Ex. 23 | C.G.P. 23 | 0.0 | 0.1 | 0.6 | 1.3 | 1.7 |
| Ex. 24 | C.G.P. 24 | 0.0 | 0.0 | 0.4 | 0.9 | 1.4 |
| Ex. 25 | C.G.P. 25 | 0.0 | 0.0 | 0.0 | 0.0 | 1.1 |
| Ex. 26 | C.G.P. 26 | 0.0 | 0.0 | 0.0 | 0.5 | 1.2 |
| Ex. 27 | C.G.P. 27 | 0.0 | 0.2 | 0.4 | 0.8 | 1.9 |
| Ex. 28 | C.G.P. 28 | 0.0 | 0.0 | 0.2 | 0.5 | 1.4 |
| Ex. 29 | C.G.P. 29 | 0.0 | 0.0 | 0.8 | 1.5 | 2.3 |
| Ex. 30 | C.G.P. 30 | 0.0 | 0.4 | 0.7 | 1.0 | 2.0 |
| Ex. 31 | C.G.P. 31 | 0.0 | 0.0 | 0.3 | 0.8 | 1.5 |
| Ex. 32 | C.G.P. 32 | 0.0 | 0.5 | 1.0 | 1.5 | 1.8 |
| Comp. Ex. 1 | G.P. F | 0.8 | 1.2 | 2.5 | 2.9 | 3.0 |

The results listed in Table 10 indicate that the granules of Comparative Example 1 initiates the release of the active ingredient immediately after the introduction thereof into water, whereas for C.G.P. Nos. 23 to 32 according to the present invention, which comprise thermosetting resins, any active ingredient is not detected, on day 1 after the introduction, clearly showing that the release of the active ingredient is initially inhibited and the active ingredient certainly undergoes controlled release in the samples of the present invention.

Moreover, the results observed for C.G.P. Nos. 23 to 25 which differ from one another in the amount of Resin 1 with respect to the thermosetting resin (Table 4) also indicate that the larger the amount of Resin 1, the later the release-initiation time of the active ingredient and that the control of the amount of Resin 1 would be effective for the adjustment of the release-suppression term.

Test for Examining Decomposition and Deterioration of Film

There was introduced, into a polypropylene nonwoven fabric having a size of 3 cm×10 cm, 10 g of each coated granular pesticide (C.G.P.) 33 to 40 (Table 5) produced in the foregoing Production Experiments. The soil in the field within a glasshouse (Tobata-Ku, Kitakyushu-Shi, Fukuoka-Ken, Japan) was digged out to a depth of 3 cm and the polypropylene nonwoven fabric was placed in the digged portion, followed by returning the soil digged out above to heap up the earth. The temperature in the glasshouse was appropriately controlled and the maximum temperature and the minimum temperature were found to be 30 and 20° C., respectively. An appropriate amount of water was supplied to the ground by sprinkling water over the ground at 8:30 and 12:30 every day using an automatic water sprinkler. These samples of the granules were taken out from the soil every two months to examine the granules for their conditions. After one year, the granules were taken out, washed with water and examined for the conditions of the films thereof. The results thus obtained are listed in the following Table 11.

TABLE 11

| Sample | | Results Observed in Film-Decomposition Test |
|---|---|---|
| Ex. 33 | C.G.P. 33 | Any change in shape was not observed even after one year. |
| Ex. 34 | C.G.P. 34 | The film was disintegrated after two months, but there was observed film residues. |
| Ex. 35 | C.G.P. 35 | The film was disintegrated after two months, and crumbled into decay upon water-washing after one year. |
| Ex. 36 | C.G.P. 36 | The film was disintegrated after two months, and crumbled into decay after 8 months. |
| Ex. 37 | C.G.P. 37 | The film was disintegrated after two months, and crumbled into decay upon water-washing after one year. |
| Ex. 38 | C.G.P. 38 | The film was disintegrated after two months, and crumbled into decay after 6 months. |
| Ex. 39 | C.G.P. 39 | The film was disintegrated after two months, and crumbled into decay upon water-washing after one year. |
| Ex. 40 | C.G.P. 40 | The film was disintegrated after two months, and crumbled into decay atter 4 months. |

As seen from the results listed in Table 11, it was confirmed that for the coated granular pesticide (C.G.P.) Nos. 35 to 40 which comprised biodegradable polymers hardly soluble or insoluble in water, the films crumbled into decay after one year and disappeared. In respect of C.G.P. Nos. 33 to 34, it was confirmed that C.G.P. No. 34 showed disintegration of the film, but the decomposition of film residues was not affected so much. The effect of decomposing the film would be ascribed to the addition of biodegradable polymers thereto and thus the reduction in the film strength would contribute to the disappearance of the film.

Test 2 for Release in Water

Figure 4:
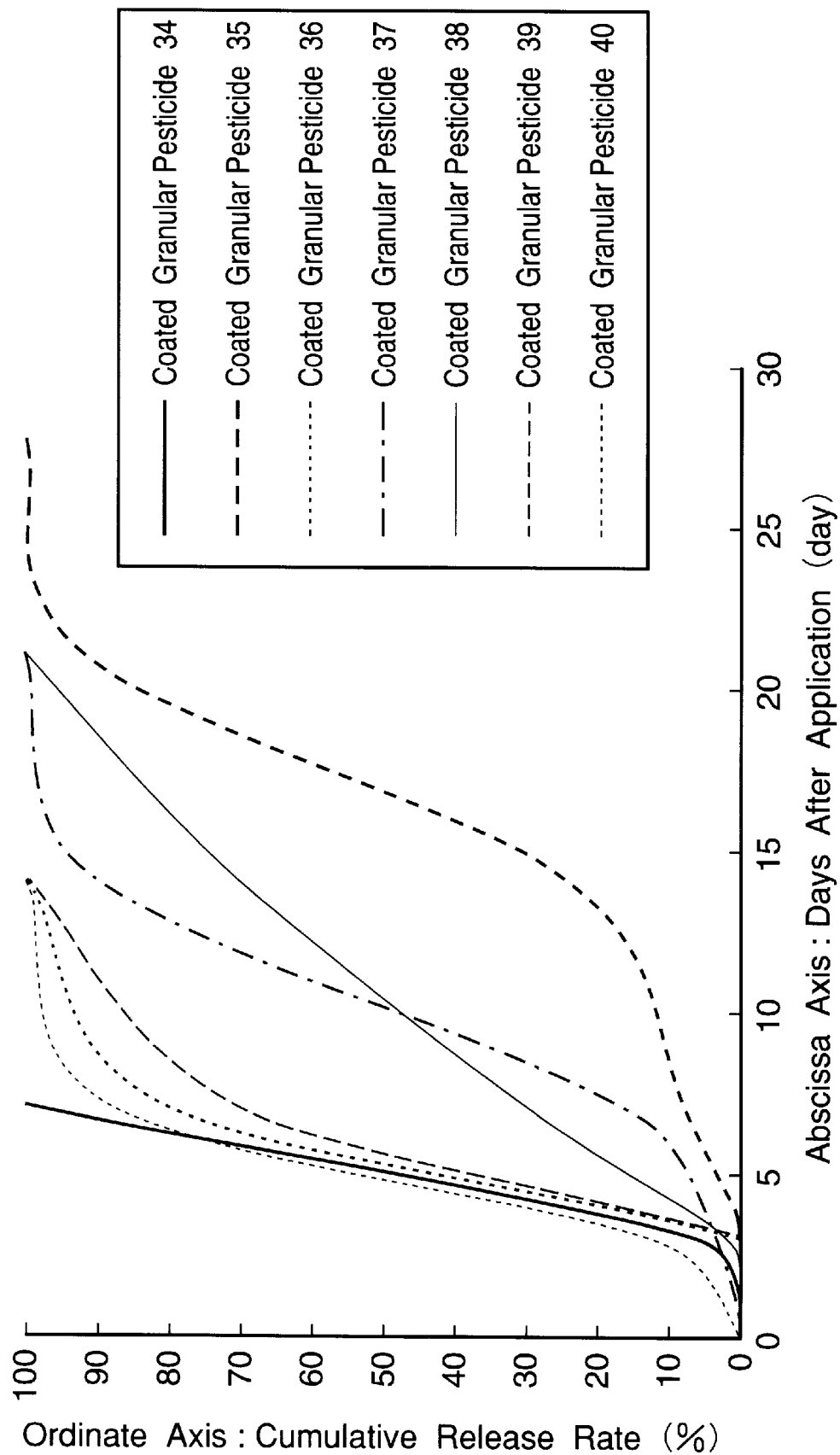
FIG. 4 is a graph showing the cumulative release percentage of the coated granular pesticides 34 to 40 over a desired period of time.

The coated granular pesticides (C.G.P.) Nos. 34 to 40 (Table 5) produced in the foregoing production experiments were subjected to tests for examining the release of the active ingredients in water. To a test tube (12 mm×72 mm) equipped with a cap, there was added 1.5 ml of water and each granular pesticide was introduced into the test tube in a rate of one granule per tube and thereafter the test tubes were capped. Using 100 test tubes (or granules) per each test division, they were allowed to stand under a predetermined condition, i.e., at a water temperature of 25° C. and the number of the granules for pesticide thus disintegrated was counted. The test tubes were observed every day for one week after the initiation of the test and thereafter the observation was carried out once a week. The results thus obtained are shown in FIG. 4. The cumulative release rate means the number of granules tested which are disintegrated.

The data shown in FIG. 4 indicate that all of the coated granular pesticides 34 to 40 exhibit almost identical release characteristics.

Test 3 for Release in Water

The coated granular pesticides (C.G.P.) Nos. 41 to 46 (Table 6) produced in the foregoing Production Experiments were subjected to tests for examining the release of the active ingredients in water. After immersing C.G.P. Nos. 41 to 46 in water maintained at 25° C., the number of days required for the 10% release of the granular pesticide (G.P.) was determined and it was defined to be release-supression term. Using 100 granules per test, the amount of the released G.P. was observed once a week to thus determine the number of G.P. granules disintegrated. The results obtained are summarized in the following Table 12.

TABLE 12

| | Sample | Release-Supression Term (Day) |
|---|---|---|
| Example 41 | C.G.P. 41 | 56 |
| Example 42 | C.G.P. 42 | 28 |
| Example 43 | C.G.P. 43 | 56 |
| Example 44 | C.G.P. 44 | 28 |
| Example 45 | C.G.P. 45 | 56 |
| Example 46 | C.G.P. 46 | 28 |

Figure 5:
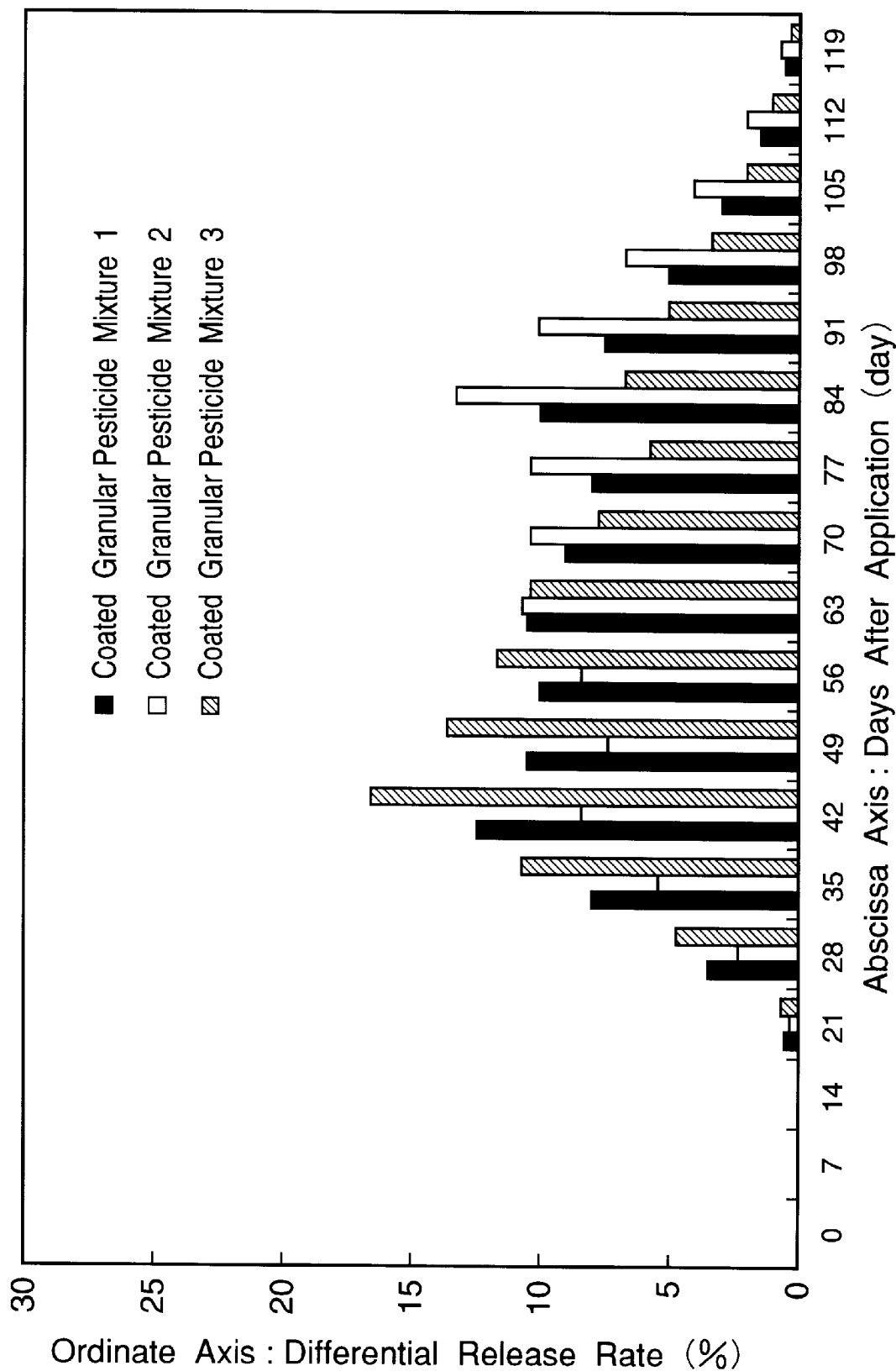
FIG. 5 is a graph showing the differential release percentage of the coated granular pesticide mixtures 1 to 3 over a desired period of time.

The coated granular pesticide (C.G.P.) mixture Nos. 1 to 3 produced in the foregoing Production Experiments were immersed in water maintained at 25° C., then the release rate of the active ingredient released from each C.G.P. was determined every 7 days to thus give an differential release rate. The differential release rate as days after application is shown in FIG. 5 as a bar graph. In addition, C.G.P. Nos. 41 and 42, each of which is a single substance, were also examined for the accumulated release rates. The resulting differential release rate as days after application is shown in FIG. 6 in the form of a bar graph.

Figure 6:
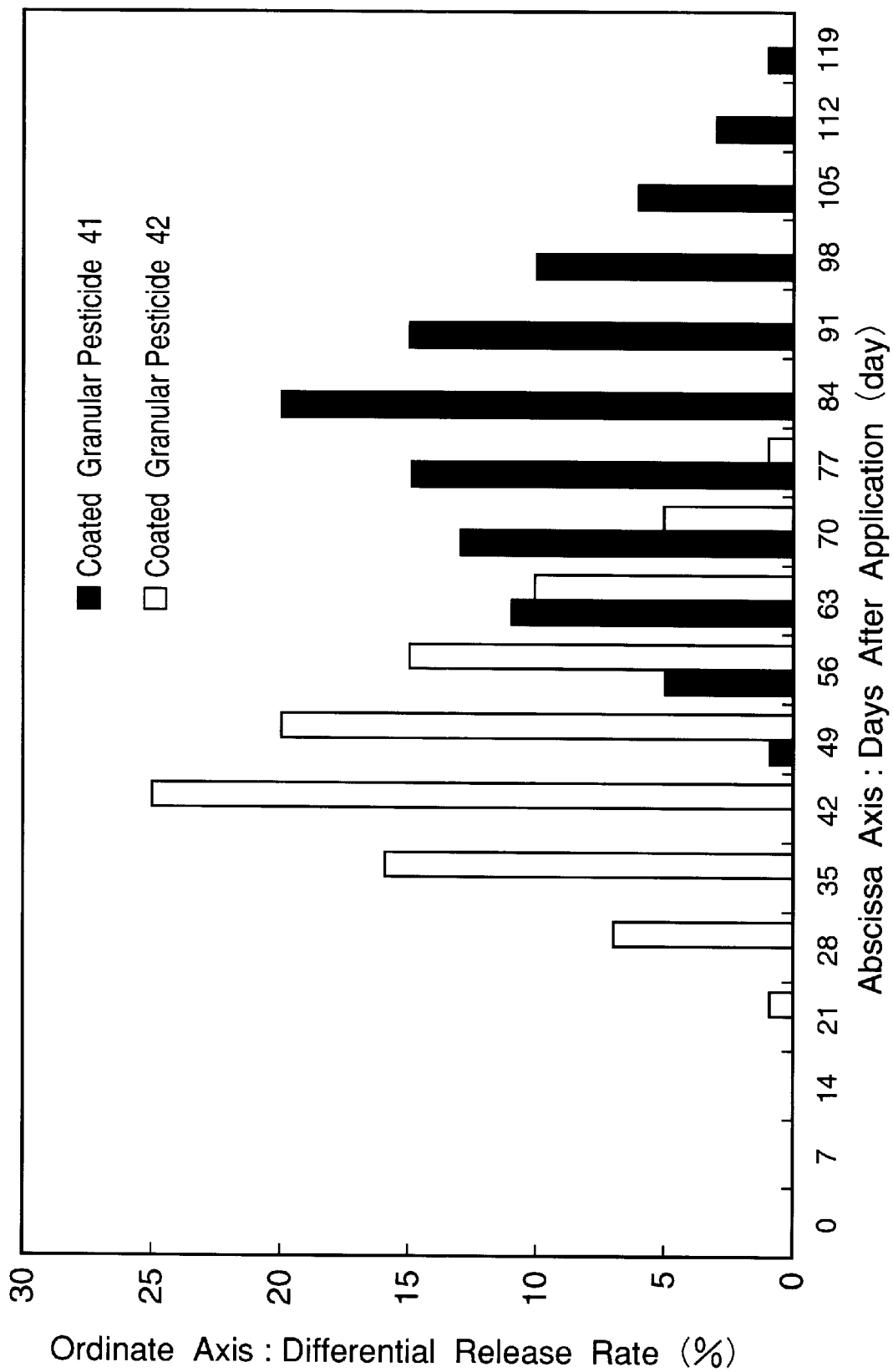
FIG. 6 is a graph showing changes, with time, in the release percentages of coated granular pesticides 41 and 42 over a desired period of time.

As has been shown in FIG. 6, each of C.G.P. Nos. 41 and 42, as single substances, has a peak of the release rate at a relatively early stage and accordingly they undergo rapid release of the active ingredients, but the duration of the release is short. On the other hand, as shown in FIG. 5, C.G.P. mixture Nos. 2 and 3 have peaks of the release rates lower than those observed for the C.G.P. Nos. 41 and 42 as single substances, but the mixtures each maintains a relatively high release rate over a long period of time, before and behind the peak. Moreover, it is found that C.G.P. mixture No. 1 does not have any particular peak, but maintains a relatively high release rate over a very long period of time.

The coated granular pesticide (C.G.P.) mixture Nos. 4 to 6 are mixtures of the coated granular pesticide (C.G.P.) Nos. 43 and 44 (they both comprise the pesticide F having an insecticidal effect). When determining the differential release rates of these mixtures, it was found that they had release terms after the film-disintegration slightly shorter than those observed for the C.G.P. mixture Nos. 1 to 3, high peaks of release rates and they exhibits initial release of trace amounts of active ingredients because of the presence of the water-soluble active ingredient F, but it was also found that they had tendencies approximately identical to those observed for the C.G.P. mixture Nos. 1 to 3.

C.G.P. mixture 7 is a mixture of the C.G.P. 41 comprising the pesticide E exhibiting a fungicidal effect and C.G.P. 43 comprising the pesticide F having an insecticidal effect. When examining the accumulated release rate of the mixture, it was found that the release rate of the mixture had a tendency almost identical to that observed for C.G.P. 45 (Table 12). It was also found that C.G.P. mixture 8 and C.G.P. 46 had approximately the same tendency. More specifically, it was found that almost the same effect could be obtained using either a coated granular pesticide produced by coating a granular pesticide which comprised active ingredients (active ingredients E and F) different in the effect such as the granular pesticide J, or a mixture comprising coated granular pesticides different from one another in the effect such as the coated granular pesticide mixture Nos. 7 and 8. In order to cope with various kinds of field crops, it is rather preferred to arbitrarily combine coated granular pesticides having different effects in such a manner that any desired effects can be obtained because of easy handling.

C.G.P. mixture 9 is a mixture whose ingredients are blended in such a manner that they can continuously release active ingredients having fungicidal effects and can release active ingredients having insecticidal effects at the later half of the growing period of field crops, and C.G.P. mixture 10 is a mixture whose ingredients are blended in such a manner that they can release active ingredients having insecticidal effects at the early half of the growing period of field crops.

Test 1 for Confirming Effect of Coated Granular Pesticide Mixture

A miniature paddy field of 1/2000a was provided in a Wagner pot and three young seedlings were transplanted to the pot to thus cultivate paddy rice (cv. Hinohikari). This cultivation of the paddy rice was carried out according to the currently used cultivation method except that the depth of water upon the transplantation was set at 3 cm. In this cultivation method, the active ingredients were used according to various methods of application and the effects the reof were evaluated. The active ingredients were used in the cultivation according to the following three methods:

Application Method A (AM: A):

A method comprises the steps of applying 0.1 g of a coated granular pesticide mixture and 0.1 g of a commercially available granular pesticide (containing 4% of the active ingredient E used in the granular pesticide H) to the side furrows of the rice seedlings simultaneously with the transplantation of the seedlings and then covering them with soil immediately after the application.

Application method B (AM: B):

A method comprises the steps of sowing seeds in a nursery box, growing to young seedlings, applying a coated granular pesticide mixture and the foregoing commercially available granular pesticide to the nursery box at this stage, wherein the amounts of these granules were adjusted so that they are equal to those used in the application method A, and then transplanting the young seedlings to a Wagner pot.

Application Method C (AM: C):

A method wherein young seedlings were transplanted without application of the coated granular pesticide mixture and the foregoing commercially available granular pesticide at all.

The coated granular pesticides (C.G.P.) 1 to 3 each was used according to the application methods A and B and the seedlings were examined for their growing conditions. As a control test division, the application method B was carried out without using any coated granular pesticide and the application method C was separately carried out as a treatment-free division, to thus examine the seedlings for their growing conditions. The results thus obtained are listed in Table 13.

TABLE 13

| | | Results of Examination |
|---|---|---|
| C.G.P. Mixture 1 | AM: A | There was not observed any lesion and chemical injury throughout the growing period. |
| | AM: B | There was not observed any lesion and chemical injury throughout the growing period. |
| C.G.P. Mixture 2 | AM: A | There was not observed any lesion and chemical injury throughout the growing period. |
| | AM: B | There was not observed any lesion and chemical injury throughout the growing period. |
| C.G.P. Mixture 3 | AM: A | There was not observed any lesion and chemical injury throughout the growing period. |
| | AM: B | There was not observed any lesion and chemical injury throughout the growing period. |
| Control Division (applied to nursery box) | | There was not observed any lesion immediately after the transplantation, but there were observed a large number of lesions after 7 weeks from the transplantation. |
| Untreated Division | | In each pot, there were observed a large number of lesions immediately after the transplantation.* |

*: Any chemical injury was not observed at all.

The data listed in Table 13 clearly indicate that the use of C.G.P. mixtures 1 to 3 by the side furrow-application (AM: A) or nursery box-application (AM: B) permits the effective control of the leaf blast and the head blast through the application thereof only one time.

Paddy Field-Application Test 1

This paddy field-application test was carried out using samples of C.G.P. 51 to 55 (Table 7) produced by the foregoing Poduction Experiments and C.G.P. mixture 11 to 16 produced by the foregoing Production Experiments.

To a Wagner pot of 1/5000a, there were added 2.5 kg of the paddy soil (collected from Minamata-Shi, Kumamoto-Ken, Japan) on which a large quantity of wild barnyard millet had grown and then water. After the pot was allowed to stand for one day, water was further added so as to be a depth of water (distance from the level of the soil to the surface of water) was 5 cm to thus establish conditions for a paddy field. In this respect, the thickness of the soil layer as measured from the bottom of the pot was found to be 10 cm. Three rice seedlings (cv. Hinohikari) which had been raised in a nursery box in advance were transplanted to each pot and 0.1 g of each sample granule was applied thereto. Separately, the granular pesticide (G.P.) F free of any coating was applied to the pot so that the application amount of the active ingredient was equal to that of each sample (Comparative Example 2). After the transplantation, the cultivation was carried out while appropriately supplementing water so as to compensate the reduced amount thereof. The cultivation was continued over 10 days and the seedlings were inspected for the presence of any chemical injury. The results thus obtained are summarized in Table 14.

Paddy Field-A--lication Test 2

Subsequent to the paddy field-application test 1, the rice plants were reaped at 10 days after the transplantation, followed by allowing the pots to stand without altering the other conditions over 40 days after the transplantation to observe growth of weeds and to thus evaluate the sustained effects of the granular pesticides. The results thus obtained are also listed in Table 14.

TABLE 14

| | Sample | Chemical Injury | Growth of Weeds[1] |
|---|---|---|---|
| Comp. Ex. 2 | G.P. F | Observed. The rice seedlings were withered within 10 days. | Weeds severely grew. |
| Ex. 47 | C.G.P. 51 | Only slight chemical injury was observed. The plant was slightly undergrown. | Weeds slightly grew. |
| Ex. 48 | C.G.P. 52 | No chemical injury was observed. | Weeds moderately grew. |
| Ex. 49 | C.G.P. 53 | No chemical injury was observed. | Weeds severely grew. |
| Ex. 50 | C.G.P. 54 | No chemical injury was observed. | Weeds severely grew. |
| Ex. 51 | C.G.P. 55 | No chemical injury was observed. | Weeds slightly grew. |
| Ex. 52 | C.G.P. Mx. 11 | No chemical injury was observed. | Weeds did not grow at all. |
| Ex. 53 | C.Q.P. Mx. 12 | No chemical injury was observed. | Weeds did not grow at all. |
| Ex. 54 | C.G.P. Mx. 13 | No chemical injury was observed. | Weeds did not grow at all. |
| Ex. 55 | C.G.P. Mx. 14 | No chemical injury was observed. | Weeds did not grow at all. |
| Ex. 56 | C.G.P. Mx. 15 | No chemical injury was observed. | Weeds did not grow at all. |
| Ex. 57 | C.G.P. Mx. 16 | No chemical injury was observed. | Weeds did not grow at all. |

[1]Weeds: Wild Barnyard Millet.

As seen from the results listed in Table 14, the granular pesticide (G.P.) F (free of any coating) caused chemical injury, while C.G.P. 51 caused only slight chemical injury, C.G.P. Nos. 52 to 55 and C.G.P. mixture Nos. 11 to 16 did not cause any chemical injury and the seedlings satisfactorily grew. This clearly indicates that if the transplantation of seedlings and the application of a herbicide are carried out at the same time, the release of the active ingredients should be inhibited over a certain period. It has been proved that the use of the coated granular pesticides according to the present invention such as C.G.P. Nos. 51 to 55 and C.G.P. mixture. Nos. 11 to 16 is quite effective for this purpose.

G.P. F and C.G.P. Nos. 51 to 55 showed herbicidal effect or weed-growth-inhibitory effect till the 30th day after the transplantation, but wild barnyard millet grew on the 40the day thereafter. This clearly indicates that the foregoing granules have an only slight residual activity. The quantity of wild barnyard millet developed was remarkable, in particular, when C.G.P. Nos. 53 to 54 were used. When using C.G.P. mixture Nos. 11 to 16, wild barnyard millet did not grow at all or scarcely grew. Therefore, it would be clearly proved that these granules showed a residual activity. These mixtures exhibited weed-growth-inhibitory effect even on and after the 40th day.

Paddy Field-Aoplication Test 3

The test was performed under the same conditions used in the foregoing paddy field-application tests 1 and 2 except that any rice seedling was not transplanted at the same period and further the opening of the pot was covered with a polyvinylidene chloride wrap to prevent the evaporation of water. The aqueous solution was periodically sampled from the center of the aqueous phase and the sample was inspected for the amount of the active ingredient. The average water temperature during the test period was 20° C. and the analysis was carried out over 40 days after the application of the pesticides. At the same time, C.G.P. Nos. 51 to 55 were also tested. As typical examples, the change in the concentration of the active ingredient of C.G.P. 55 present in the water is shown in FIG. 7 and those observed for C.G.P. mixture Nos. 11 to 16 are shown in FIG. 8.

Figure 7:
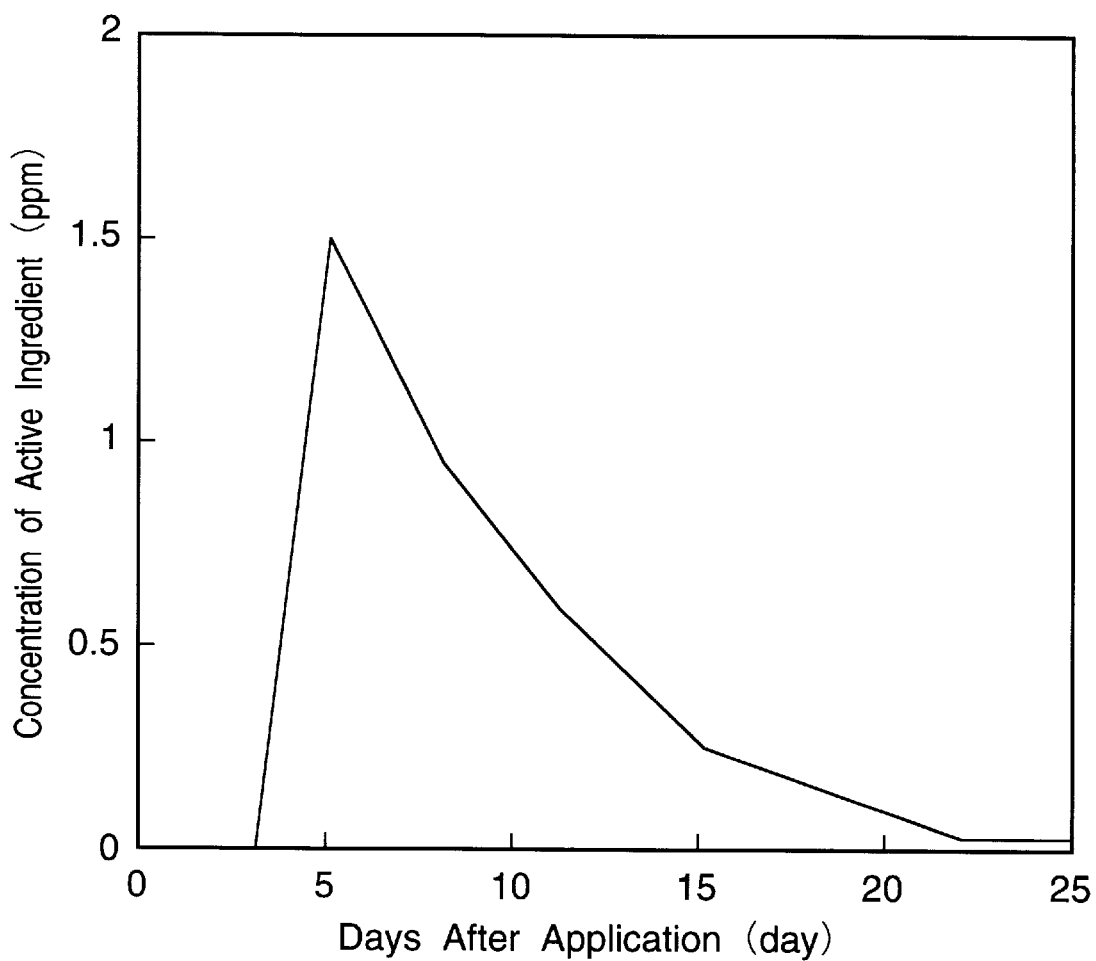
FIG. 7 is a graph showing the change, with time, in the cocenntration of the active ingredient of the coated granular pesticide 55 (early-release-initiating type coated granular herbicide) in water.
Figure 8:
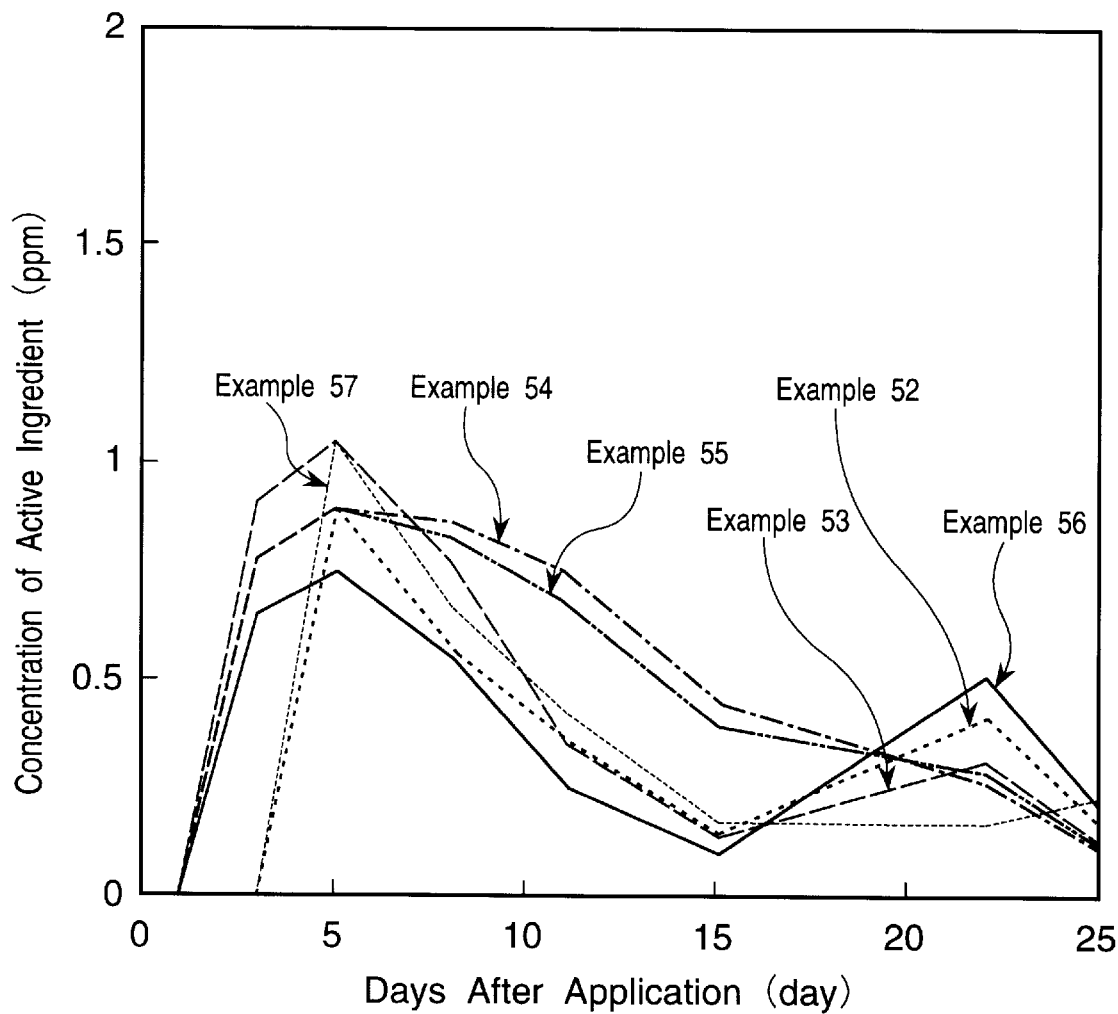
FIG. 8 is a graph showing changes, with time, in the concentration of the active ngredients of the coated granular pesticide mixtures 11 to 16 in water.

The data plotted on FIG. 7 indicate that C.G.P. 55 is an early release-initiation type coated granular herbicide, it is confirmed that the release of the active ingredient is inhibited for 3 days and thereafter the active ingredient is rapidly released and discharged in water. In addition, the concentration of the active ingredient is reduced on the 20th day after the application of the granule and thus it would be assumed that the granule would lose the efficacy. The results shown in FIG. 8 clearly indicate that C.G.P. mixture Nos. 11 to 16 permit the maintenance of each active ingredient's concentration to a desired level and the efficacy thereof lasts over a long period of time, although the amount of each C.G.P. mixture 11 to 16 is identical to those of the G.P. F and C.G.P. Nos. 51 to 55.

Test 3 for Release in Water

C.G.P. 47 and 48 (Table 6) produced in the foregoing Production Experiments were subjected to tests for examining the release of the active ingredients in water. There were added, to a beaker, 1000 ml of distilled water and 0.1 g of each C.G.P. and each C.G.P. was inspected for the film disintegration conditions with the lapse of time. In addition, the distilled water in the beaker was periodically sampled, followed by analyzing the hardly water-soluble active ingredients present in the sampled distilled water using high performance liquid chromatography and detection of the peak to thus determine the release initiation time. The water temperature during the determination was set at 25° C. and the determination was carried out over 28 days after the application of the granule. The results obtained are summarized in the following Table 15.

Test 4 for Release in Water

C.G.P. 49 and 50 produced in the foregoing production experiments were subjected to tests for examining the release of the active ingredients in water. There were added, to a beaker, 500 ml of distilled water and 1 g of each C.G.P. and each C.G.P. was inspected for the film disintegration conditions with the lapse of time. In addition, the distilled water in the beaker was periodically sampled, followed by analyzing the hardly water-soluble active ingredients present in the distilled water thus sampled using high performance liquid chromatography and detection of the peak to thus determine the release-initiation time. The water temperature during the determination was set at 25° C. and the determination was carried out over 35 days after the application of the granule. The results obtained are also summarized in the following Table 15.

TABLE 15

| | Sample | Release-Initiation Time (Day) |
|---|---|---|
| Example 58 | C.G.P. 47 | 20th |
| Example 59 | C.G.P. 48 | 20th |
| Example 60 | C.G.P. 49 | 30th |
| Example 61 | C.G.P. 50 | 18th day after the application |

Production of Substrate for Raising Seedlings

Substrate 1 for Raising Seedlings

To a concrete mixer, there were added a mixture of 2900 g of diluvial volcanic ash soil (maximum water-holding capacity: 120%; particle size: not more than 2 mm) and 100 g of vermiculite (particle size: not more than 10 mm) as a water-holding material (3000 g in total); compound fertilizer (N-$P_2O_5$-$K_2O$=13-13-13, Chisso Corporation, trade name: Kumiai Ryuukarinan No. 11) in such an amount that the amounts of N, $P_2O_5$ and $K_2O$ each was equal to 1 g, as a fertilizer for raising seedlings; and 50 g of C.G.P. 47 produced in the foregoing production experiment, followed by admixing these ingredients till a uniform mixture was obtained to give a substrate for raising seedlings of a paddy rice.

Substrate 2 for Raising Seedlings

The same procedures used for preparing the substrate 1 for raising seedlings except for using a blend containing 50 g of coated compound fertilizer (N-$P_2O_5$-$K_2O$=14-12-14, Asahi Chemical Industry Co., Ltd., trade name: Long 424) and Ryuukarinan as a quick-acting fertilizer for raising seedlings in such an amount that the amounts of N, $P_2O_5$ and $K_2O$ each was equal to 1 g, in place of the fertilizer used in the substrate 1 to thus give a substrate for raising seedlings of a paddy rice.

Substrate 3 for Raising Seedlings

To a concrete mixer, there were added 3000 g of diluvial volcanic ash soil (maximum water-holding capacity: 120%; particle size: not more than 2 mm) as a water-holding material and Ryuukarinan as a quick-acting fertilizer for raising seedlings in such an amount that the amounts of N, $P_2O_5$ and $K_2O$ each was equal to 1 g, followed by admixing these ingredients till a uniform mixture was obtained to thus give a substrate for raising seedlings of a paddy rice.

Substrate 4 for Raising Seedlings

To a concrete mixer, there were added 3000 g of diluvial volcanic ash soil (maximum water-holding capacity: 120%; particle size: not more than 2 mm) as a water-holding material and compound fertilizer (N-$P_2O_5$-$K_2O$=13-13-13, Chisso Corporation, trade name: Kumiai Ryuukarinan No. 11) as a fertilizer for raising seedlings in such an amount that the amounts of N, $P_2O_5$ and $K_2O$ each was equal to 1 g, followed by admixing these ingredients till a uniform mixture was obtained to thus give a substrate for raising seedlings of a paddy rice.

Substrate 5 for Raising Seedlings

To a concrete mixer, there were added 3000 g of diluvial volcanic ash soil (maximum water-holding capacity: 120%; particle size: not more than 2 mm) as a water-holding material, compound fertilizer (N-$P_2O_5$-$K_2O$=13-13-13, Chisso Corporation, trade name: Kumiai Ryuukarinan No. 11) as a fertilizer for raising seedlings in such an amount that the amounts of N, $P_2O_5$ and $K_2O$ each was equal to 1 g and 50 g of the coated granular pesticide 48 produced in the foregoing Production Experiment, followed by admixing these ingredients till a uniform mixture was obtained to thus give a substrate for raising seedlings of a paddy rice.

Substrate 6 for Raising Seedlings

A substrate for single cell transplanting, "Yosaku N-150" (Kyushu Chemical Industry Co., Ltd.), comprising vermiculite and peat-moss as principal components was used as the water-holding material. This water-holding material has such physico-chemical properties as an apparent specific gravity of 0.38 kg/L, a pH value (1:5 water) of 6.7, an electric conductivity (EC) (1:5 water) of 0.7 mS/cm and a water content of 30% and the contents of fertilizer components are 150 mg/L of N, 1000 mg/L of $P_2O_5$ and 150 mg/L of $K_2O$. Among these, all of the ammonium nitrogen is originated from acetaldehyde-condensed urea (CDU). Furthermore, it also comprised citric acid-soluble MnO and $B_2O_3$ in amounts of 0.2 mg/kg and 0.05 mg/kg, respectively.

A 9 cm plastic pot (having inner volume of about 300 ml) was filled with the mixture containing the water-holding material, followed by applying 1 g of C.G.P. 49 produced in the foregoing production experiment on the mixture and then stirring it to give a substrate for vegetable.

Substrate 7 for Raising Seedlings

A water-holding material was produced by a vermiculite-substrate for horticulture, "Yosaku No. V1" (Kyushu Chemical Industry Co., Ltd.), comprising vermiculite and peat-moss as principal components, and disinfected diluvial volcanic ash soil (maximum water-holding capacity: 120%; particle size: not more than 2 mm) in a volume ratio of 1:3 and then uniformly mixing these ingredients. This vermiculite-substrate for horticulture has such physico-chemical properties as an apparent specific gravity of 0.35 kg/L, a pH value (1:5 water) of 6.8, an EC value (1:5 water) of 1.3 mS/cm and a water content of 30% and the contents of fertilizer components are 500 mg/L of N, 4400 mg/L of $P_2O_5$ and 400 mg/L of $K_2O$. In this respect, 300 mg/L of the nitrogen is originated from acetaldehyde-condensed urea (CDU) and 200 mg/L of the ammonium nitrogen. Furthermore, it also comprised citric acid-soluble MnO and $B_2O_3$ in amounts of 0.2 mg/kg and 0.05 mg/kg, respectively.

A 9 cm plastic pot (having inner volume of about 300 ml) was filled with the mixed soil, followed by applying 1 g of C.G.P. 49 produced in the foregoing Production Experiment on the mixed substrate and then stirring it to give a substrate for vegetable.

Substrate 8 for Raising Seedlings

A substrate for vegetable growing was produced by the same procedures used in the production of the substrate 7 for raising seedlings except that there was applied, to the substrate 7 for raising seedlings, 1 g of a coated compound fertilizer, "Micro Long Total 201-100" (Asahi Chemical Industry Co., Ltd.) and that the resulting mixture was then uniformly stirred.

Substrate 9 for Raising Seedlings (Comparative)

Disinfected diluvial volcanic ash soil (maximum water-holding capacity: 120%; particle size: not more than 2 mm) was used and fertilizer components were added so that each pot comprised 150 mg/L of N, 1000 mg/L of $P_2O_5$ and 150 mg/L of $K_2O$. Micro elements included therein were water-soluble MnO and $B_2O_3$ whose contents were 0.2 mg/kg and 0.05 mg/kg, respectively.

A 9 cm plastic pot (having inner volume of about 300 ml) was filled with the foregoing mixture containing the water-holding material to give a substrate for vegetable.

Substrate 10 for Raising Seedlings

A substrate for vegetable was produced according to the same procedures used for producing the substrate 6 for raising seedlings except that C.G.P. 49 was not incorporated into the substrate.

Substrate 11 for Raising Seedlings

A substrate for single cell transplanting, "Yosaku N-100" (Kyushu Chemical Industry Co., Ltd.), comprising vermiculite, peat-moss and perlite as principal components was used as the water-holding material. This water-holding material has such physico-chemical properties as an apparent specific gravity of 0.38 kg/L, a pH value (1:5 water) of 6.3, an EC value (1:5 water) of 0.5 mS/cm and a water content of 40% and the contents of fertilizer components are 100 mg/L of N, 500 mg/L of $P_2O_5$ and 100 mg/L of $K_2O$. Among these, all of the nitrogen is originated from acetaldehyde-condensed urea (CDU). Furthermore, it also comprised citric acid-soluble MnO and $B_2O_3$ in amounts of 0.2 mg/kg and 0.05 mg/kg, respectively. In addition, 2 g of C.G.P. 50 produced in the foregoing production experiment was applyed on the mixture and then the mixture was stirred to give a substrate for flowers and ornamental plants.

Substrate 12 for Raising Seedlings

A substrate for flower growing was produced according to the same procedures used for producing the substrate 11 for raising seedlings except that C.G.P. 50 was not incorporated into the substrate.

Raising Seedling Test

Example 62

The substrate 1 for raising seedlings (2000 g) was introduced into a nursery box, followed by smoothing the surface of the substrate and uniformly sowing 150 g of rice seeds of a paddy rice (cv. Hinohikari) in the substrate. Moreover, the seeds were covered with 1000 g of the same substrate. Thereafter the nursery boxes were placed in a glasshouse (Tobata-Ku, Kitakyushu-Shi, Fukuoka-Ken, Japan) to thus grow young seedlings. The cultivation management was performed by appropriately watering to prevent drying of the superficial layer of the substrate and carrying out additional manure two times, i.e., applying 0.5 g each (as expressed in terms of the amount of N) of the foregoing Ryuukarinan (twice) per nursery box. Other management for raising seedlings was carried out according to the methods currently used.

Example 63

A raising seedling test was carried out according to the same procedures used in Example 62 except that the substrate 2 for raising seedlings was substituted for the substrate 1 for raising seedlings and that the additional manure was omitted.

Example 64

The substrate 3 for raising seedlings (2000 g) was introduced into a nursery box, followed by smoothing the surface of the substrate and uniformly sowing the substrate with a mixture comprising 150 g of rice seeds of a paddy rice (cv. Hinohikari) and 600 g of coated urea (N-$P_2O_5$-$K_2O$=40-0-0, Chisso Corporation, trade name: LP Coat S100) showing sigmoid type fertilizer-release characteristics. The soil cover used was a composition produced by uniformly mixing 1000 g of the same substrate with 50 g of C.G.P. 47 produced in the foregoing Production Experiment. Thereafter the nursery boxes were placed in the same glasshouse used in Example 62 to thus grow young seedlings. The cultivation management was performed by appropriately watering to prevent drying of the superficial layer of the substrate and additional manure was omitted. Other management for raising seedlings was carried out by the same procedures used in Example 62.

Comparative Example 3

A substrate (2000 g) produced by uniformly mixing 3000 g of the substrate 4 for raising seedlings with 34.5 g of the granular pesticide K produced in the foregoing poduction experiment was introduced into a nursery box, followed by smoothing the surface of the substrate and uniformly sowing 150 g of rice seeds of a paddy rice (cv. Hinohikari) in the substrate. The same substrate (1000 g) was used as the soil cover. Thereafter the nursery boxes were placed in the same glasshouse used in Example 62 to thus grow young seedlings. The cultivation management was performed by appropriately watering to prevent drying of the superficial layer of the substrate and carrying out additional manure two times, i.e., applying 0.5 g each (as expressed in terms of the amount of N) of the foregoing Ryuukarinan (twice) per nursery box. Other management for raising seedlings was carried out by the same procedures used in Example 62.

Example 65

The substrate 5 for raising seedlings (2000 g) was introduced into a nursery box, followed by smoothing the surface of the substrate and uniformly sowing 150 g of rice seeds of a paddy rice (cv. Hinohikari) in the substrate. Moreover, the seeds were covered with 1000 g of the same substrate 5. Thereafter the nursery boxes were placed in the same glasshouse used in Example 62 to thus grow young seedlings. The cultivation management was performed by appropriately watering to prevent drying of the superficial layer of the substrate and carrying out additional manure two times, i.e., applying 0.5 g each (as expressed in terms of the amount of N) of the foregoing Ryuukarinan (twice) per nursery box. Other management for raising seedlings was carried out according to the currently used method.

Comparative Example 4

The substrate 4 for raising seedlings was introduced into a nursery box and the granular pesticide L produced in the foregoing production experiments was applied to the substrate in the nursery box immediately before transplantation of seedlings according to the currently used method. Thereafter the nursery boxes were placed in the same glasshouse used in Example 62 to thus grow young seedlings. The cultivation management was performed according to the currently used method.

Triplicate divisions treated according to each method disclosed in Example 62 to 65 or Comparative Example 3 or 4 were examined for chemical injury during the seedling-raising term. The results thus obtained are listed in Table 16.

TABLE 16

| Sample (Substrate for Raising) | Day after sowing (Day) | | | | |
|---|---|---|---|---|---|
| | 1 | 3 | 7 | 14 | 21 |
| Ex. 62 | 1 | --- | --- | --- | --- | --- |
| Ex. 63 | 2 | --- | --- | --- | --- | --- |
| Ex. 64 | 3 | --- | --- | --- | --- | --- |
| Ex. 65 | 5 | --- | --- | --- | --- | --- |
| Comp. Ex. 3 | 4 | --- | ±±± | ±±± | +++ | +++ |
| Comp. Ex. 4 | 4 | --- | --- | --- | --- | --- |

–: Any chemical injury was not observed.

±: There was observed slight chemical injury, but any practical problem did not arise.

+: There was observed chemical injury.

As seen from the results shown in Table 16, seedlings could satisfactorily be raised in Examples 62 to 65 and Comparative Example 4 without causing any chemical injury. In Comparative Example 3, a growth-inhibitory effect was observed shortly after the application of the pesticide and it has thus been proved that the seedlings were damaged from the pesticide and that the formulation prepared by such a conventional method is not favorably used as a substrate for raising seedlings of a paddy rice. Moreover, it was also confirmed that good seedlings could satisfactorily be raised without being damaged from the pesticide during the raising term in Example 65 wherein a different active ingredient was used.

Paddy Rice Cultivation Test I

Young seedlings of a paddy rice were raised over 3 weeks according to the procedures disclosed in either of Examples 62 to 64 and Comparative Example 3 and then the young seedlings were transplanted to and cultivated in each Wagner pot of 1/2000a at a rate of three seedlings per pot. The cultivation was carried out according to the currently used method except that the depth of water upon the transplantation was set at a level of 3 cm. Regarding the test divisions of Comparative Example 3, the granular pesticide K was applied thereto on the 7the day after the transplantation.

As a result, the observation of the seedlings throughout the cultivation term proved that the efficacies of the active ingredients observed in Examples 62 to 64 were identical to or superior to that observed in Comparative Example 3 and that barnyard millet at its bifoliate period was controlled in both Examples 62 to 64 and Comparative Example 3. In particular, the seedlings in Example 64 did not require any additional manure during the cultivation period. Accordingly, this would considerably contribute to the reduction of labor required for application of pesticides and/or fertilizers.

Paddy Rice Cultivation Test II

Young seedlings of a paddy rice were raised over 3 weeks according to the procedures disclosed in either of Example 65 and Comparative Example 4 and then cultivation tests were carried out using 30 bundles (3 stocks/bundle) selected from 5 among the foregoing nursery boxes. In the tests, the transplantation and cultivation were carried out using Wagner pots of 1/5000a under paddy conditions (depth of water: 3 cm).

As a result, there was observed irregularity in the efficacy of the granular pesticide L in Comparative Example 4 and part of the leaves were damaged from the active ingredient of the pesticide L adhered thereto. This fact proves that it is difficult to uniformly apply the granular pesticide L as a conventional pesticide on the nursery boxes comprising seedlings of paddy rice which has grown to some extent and whose leaves have grown thick. Both Example 65 and Comparative Example 4 exhibited sufficient efficacies and, in particular, Example 65 showed a duration of efficacy longer than that observed in Comparative Example 4.

Test for Confirming Effects Using Cucumber

A test for raising seedling and cultivation of cucumber (cv. Kinseishiyo No. 2; "KURUME GENSHU IKUSEI KAI (Society of Kurume-Foundation Stock Growth)") was carried out using the substrates 6 to 10 for raising seedlings as substrate for vegetable. The raising seedlings and the cultivation thereof were carried out in a glasshouse (Tobata-Ku, Kitakyushu-Shi, Fukuoka-Ken, Japan) and the management for raising of seedlings and cultivation thereof was carried out according to the methods currently used.

In every test divisions other than the substrate 8 for raising seedlings, additional manure was carried out several times during the raising of seedlings. The raising seedlings was terminated after 30 days and then the seedlings were transplanted to Wagner pots of 1/2000a filled with disinfected diluvial volcanic ash soil. The substrate 10 for raising seedlings was subjected to the hole treatment according to the currently used method using 1 g of kneaded granules containing 2% of an active ingredient (pesticide C). The test was carried out four times using 3 stocks per each test division and each test division was observed and examined. The results thus obtained are summarized in the following Table 17.

TABLE 17

| Sample | Examination of Plant (after 2 weeks) | | Status After 3 Weeks from the Transplantation of Seedlings |
|---|---|---|---|
| (No. of Substrate) | Length (cm) | No. of Leaves | |
| Ex. 66 | 7 | 19.2 | 2.5 | There was not observed any chemical injury; there was not observed any breeding of aphids. |
| Ex. 67 | 8 | 21.5 | 2.5 | There was not observed any chemical injury; there was not observed any breeding of aphids. |
| Ex. 68 | 9 | 22.0 | 2.5 | There was not observed any chemical injury; there was not observed any breeding of aphids. |
| Comp. Ex. 5 | 10 | 19.5 | 3.0 | There was observed the breeding of aphids. |
| Comp. Ex. 6 | 11 | 20.8 | 3.0 | There was not observed any chemical injury; there was not observed any breeding of aphids. |

As seen from the results listed in Table 17, the substrates 6 to 8 for raising seedlings permitted satisfactory raising and cultivation of seedlings without causing any damage from the pesticide throughout the cultivation period including that required for raising the seedlings. On the other hand, in case of the substrate 9 for raising seedlings, aphids came flying immediately after the transplantation and the seedlings suffered from disease injury. There were observed dead aphids in the vicinity of the stocks transplanted to the substrates 6 to 8 and 10 and accordingly, the efficacies of the pesticides would be sufficient in these substrates.

In addition, there was observed a tendency of suffering from micro element (iodine)-excess symptom on the seedlings transplanted to the substrate 9. This would be caused due to the water-solubility of the micro element, but the excess symptom could be ignored from the viewpoint of cultivation.

The substrates 6 to 8 can eliminate the use of the hole treatment and therefore, the transplantation operation of the seedlings required only a short period of time. The substrate 10 required a great deal of labor since the substrate 10 required the use of the hole treatment and the use of this substrate further required additional operations for weighing and applying the granular pesticide in addition to the operations required for digging holes.

Effect-Confirmation Test Using Chrysanthemum

Tests for raising seedlings of chrysanthemum and for cultivating thereof were carried out using the substrates 11 and 12 for raising seedlings. The chrysanthemum to be tested (cv. Oki No Shiranami) was subjected to herbaceous cutting in a cell tray (circular connected tray having an upper diameter of 23 mm, a bottom diameter of 18 mm, a depth of 35 mm and a volume of 12 ml) and the seedlings were raised under the lighting conditions. The raising seedlings and the cultivation thereof were carried out in a glasshouse (Tobata-Ku, Kitakyushu-Shi, Fukuoka-Ken, Japan) and the management of the raising seedlings and the cultivation thereof were performed according to the currently used methods. In every test divisions, additional manure was carried out several times during the raising seedlings. The raising seedlings was terminated after 2 weeks at which the roots of the seedlings had grown to densely fill the substrate in the cell and then the seedlings were transplanted to Wagner pots of 1/2000a filled with disinfected diluvial volcanic ash soil (the pH value thereof was adjusted to 6.3). The substrate 13 for raising seedlings was subjected to the hole treatment according to the currently used method using 2 g of kneaded granules (containing 0.5% by weight of an active ingredient of the pesticide C). The cultivation test was carried out four times using 3 stocks per each test division and each test division was observed and examined. The results thus obtained are summarized in the following Table 18.

TABLE 18

|  | Substrate for Raising Seedling No. | Results Observed after One Week from the Transplantation |
|---|---|---|
| Example 69 | 12 | There was not observed any damage from pesticide. Aphids were exterminated. |
| Comp. Example 7 | 13 | There was not observed any damage from pesticide. Aphids were exterminated. |

As will be clear from the results listed in Table 18, the substrate 11 for raising seedlings permitted satisfactory raising and cultivation of seedlings without causing any damage from the pesticide through out the cultivation period including that required for raising the seedlings. There were observed dead aphids in the vicinity of the stocks transplanted to the substrates 11 to 12 and accordingly, the efficacies of the pesticides would be sufficient in these substrates. The substrate 11 did not require the use of the hole treatment and the seedlings were raised in a cell tray filled with the substrate 11. Therefore, the transplantation operation of a large number of the seedlings required only a short period of time and this results in a substantial reduction of labor. The substrate 12 required a great deal of labor since the substrate 12 required the use of the hole treatment and the use of this substrate further required additional operations for weighing and applying the granular pesticide in addition to the operations required for digging holes.

Effects of the Invention

As has been explained above in detail, the coated granular pesticide according to the present invention can initiate the release of the active ingredient of the pesticide after the lapse of a predetermined time, since a film of a thermoplastic resin is formed on the surface of a granular pesticide which comprises a hardly water-soluble active ingredient and a water-swelling substance. More specifically, the following effects can be accomplished by the present invention.

(1) The conventional pesticide comes in contact with the environmental water simultaneous with the application thereof and therefore, it initiates the release of the active ingredient thereof immediately after the application. On the other hand, the coated granular pesticide of the present invention permits the inhibition of the release of the hardly water-soluble active ingredient of the pesticide over a predetermined period of time.

(2) The conventional coated granular pesticide releases the active ingredient of the pesticide through migration of water while making use of the permeability of the film instead of making use of the disintegration of the film. Accordingly, such conventional technique is not effectively applied to pesticides comprising hardly water-soluble active ingredients. Contrary to this, the coated granular pesticide of the present invention permits the external release of the active ingredient through the disintegration of the film due to the co-operated interaction of the water permeability of the film and the water-swelling properties of the water-swelling substance present in the granular pesticide. For this reason, the present invention permits the use of hardly water-soluble active ingredients and thus the present invention can make the range of choice of usable active ingredients more wider.

(3) The coated granular pesticide of the present invention permits the release of the granular pesticide containing the hardly water-soluble active ingredient through the disintegration of the film thereof. Therefore, the pesticide does not result in the reduction of the release rate as the concentration on the active ingredient in the aqueous solution within the film is reduced and the active ingredient does not remain within the film over a long time period, unlike the conventional controlled release type coated granular pesticides, and the coated pesticide of the present invention can completely release the hardly water-soluble active ingredient, ensure a high utilization factor and is not accompanied by any danger due to residues. Moreover, the present invention also permits the reduction of the amount of the hardly water-soluble active ingredient to be used.

(4) The use of a mixture of at least two coated granular pesticides which differ in the release-inhibitory period permits the sustained release of required active ingredients over a long period of time depending on the kinds of field crops.

(5) The present invention can inhibit the appearance of any peak of the released active ingredient and accordingly, can prevent any damage of field crops from the pesticide due to temporary excess release of the active ingredient.

(6) The conventional insecticides and/or fungicides must be applied to field crops several times during the whole growth period thereof, while if the coated granular pesticide mixture of the present invention is used, any desired effect can be obtained by a single application thereof to the crops and the present invention can thus further reduce labor required for farm working. With respect to the paddy rice, in particular, both leaf blast and head blast can be controlled by a single application of the foregoing mixture.

(7) In the present invention, it is very easy to control the release rate of the active ingredient by appropriately selecting components to be added to the film.

(8) The substrate for raising seedlings according to the present invention which can be prepared by admixing the coated granular pesticide, a water-holding material and optionally a fertilizer or the like can easily be handled, is effective for the reduction of labor required for farm working and is quite useful as substrates for raising seedlings of paddy rice and substrates for raising seedlings used for other agricultural and/or horticultural purposes.

What is claimed is:

1. A coated granular pesticide, said coated granular pesticide comprising at least one hardly water-soluble active ingredient and at least one water-swelling substance which have been mixed together and then formed into granules, the surface of said granular pesticide being coated with a film whose principal component is a thermoplastic resin, wherein said thermoplastic resin is selected from the group consisting of at least one polyolefin, an olefinic copolymer including olefin monomers, and mixtures thereof.

2. The coated granular pesticide as set forth in claim 1 wherein an ethylene/vinyl acetate copolymer is incorporated into the film in an amount of not more than 15% by weight.

3. The coated granular pesticide as set forth in claim 1 wherein a surfactant is incorporated into the film.

4. The coated granular pesticide as set forth in claim 1 wherein a thermosetting resin is incorporated into the film.

5. The coated granular pesticide as set forth in claim 1 wherein a biodegradable polymer insoluble or hardly soluble in water is incorporated into the film.

6. The coated granular pesticide as set forth in claim 1 wherein the hardly water-soluble active ingredient is an active ingredient for pesticide having insecticidal and/or fungicidal effects.

7. The coated granular pesticide as set forth in claim 1 wherein the hardly water-soluble active ingredient is an active ingredient for pesticide having a herbicidal effect.

8. The coated granular pesticide as set forth in claim 1 wherein the film has a single layer structure.

9. The coated granular pesticide as set forth in claim 1 wherein said pesticide can externally release the hardly water-soluble active ingredient thereof according to such a mechanism that the water-swelling substance absorbs water from the external environment, which gradually penetrates into the active ingredient through the coating film, the granular pesticide containing the water-swelling substance gradually expands, cracks are thus formed on the film after the elapse of a predetermined time, water rapidly enters into the active ingredient through the cracks thus formed, the swelling of the water-swelling substance is accelerated to thus greatly grow the cracks and to thus rapidly disintegrate the film and that the hardly water-soluble active ingredient included in the granular pesticide thus comes in close contact with a large amount of water.

10. A coated granular pesticide, said coated granular pesticide comprising at least one hardly water-soluble active ingredient and at least one water-swelling substance which have been mixed together and then formed into granules, the surface of said granular pesticide being coated with a film whose principal component is a thermoplastic resin, wherein an inorganic powder which is insoluble or hardly soluble in water, is incorporated into the film.

11. A coated granular pesticides, said coated granular pesticide comprising at least one hardly water-soluble active ingredient and at least one water-swelling substance which have been mixed together and then formed into granules, the surface of said granular pesticide being coated with a film whose principal component is a thermoplastic resin, wherein at least one of a water absorbing polymer fine powder or water-soluble polymer fine powder is incorporated into the film.

12. A coated granular pesticide according to claim 1, wherein said mixture of the at least one hardly water-soluble active ingredient and at least one water-swelling substance are mixed so as to form a blend and the blend is then coated with said film.

13. A coated granular pesticide according to claim 1, wherein said granules are formed by extrusion.

14. A coated granular pesticide according to claim 1, wherein said hardly water-soluble active ingredient and said water-swelling substance are mixed together to form a blend in such manner that the pesticide will continuously release active ingredients.

* * * * *